(12) United States Patent
Robakis et al.

(10) Patent No.: US 7,884,067 B2
(45) Date of Patent: Feb. 8, 2011

(54) PEPTIDES DERIVED FROM CADHERIN AND METHODS OF USE THEREOF

(75) Inventors: Nikolaos Robakis, Leonia, NJ (US); Philippe Marambaud, New York, NY (US); Anastasios Georgakopoulos, New York, NY (US)

(73) Assignee: Mount Sinai School of Medicine of New York University, New York, NY (US)

( * ) Notice: Subject to any disclaimer, the term of this patent is extended or adjusted under 35 U.S.C. 154(b) by 1248 days.

(21) Appl. No.: 10/509,170

(22) PCT Filed: Apr. 10, 2003

(86) PCT No.: PCT/US03/11359

§ 371 (c)(1),
(2), (4) Date: May 19, 2005

(87) PCT Pub. No.: WO03/087136

PCT Pub. Date: Oct. 23, 2003

(65) Prior Publication Data

US 2005/0245453 A1  Nov. 3, 2005

Related U.S. Application Data

(60) Provisional application No. 60/327,617, filed on Oct. 5, 2001.

(51) Int. Cl.
*A61K 38/10* (2006.01)

(52) U.S. Cl. .............................. 514/2; 514/14; 435/23; 530/326

(58) Field of Classification Search ........................ None
See application file for complete search history.

(56) References Cited

U.S. PATENT DOCUMENTS

| 5,766,846 | A | 6/1998 | Schlossmacher et al. |
| 6,284,221 | B1 | 9/2001 | Schenk et al. |
| 6,346,512 | B1 | 2/2002 | Blaschuk et al. |
| 6,358,920 | B1 | 3/2002 | Blaschuk et al. |
| 6,359,112 | B2 | 3/2002 | Kapurniotu et al. |
| 6,787,136 | B1 * | 9/2004 | Brenner et al. ........... 424/145.1 |

OTHER PUBLICATIONS

Strooper et al., Nature, 1998, vol. 391, pp. 387-390.*
Antul et al. (2002) *Neurobiology of Disease* 9:269-273.
Baki et al. (2001) *Proc. Natl. Acad. Sci. USA* 98:2381-2386.
Chen et al. (2002) *J. Biol. Chem.* 277:36521-36526.
DeStrooper et al. (1998) *Nature* 391:387-390.
Georgakopoulos et al. (1999) *Molecular Cell* 4:893-902.

* cited by examiner

*Primary Examiner*—Christopher R. Tate
*Assistant Examiner*—Roy Teller
(74) *Attorney, Agent, or Firm*—Fox Rothechild LLP

(57) ABSTRACT

The present invention provides polypeptides and peptides derived from cadherin. The polypeptides and peptides are useful in a method of inhibiting amyloid deposition and a method of inhibiting tumor metastasis. A method of determining susceptibility to Alzheimer's disease and a method of screening for agents that modify cadherin processing are also provided.

4 Claims, 20 Drawing Sheets

Abeta 40

* p< 0.0001    n=5, each triplicate

PEPTIDES DERIVED FROM CADHERIN AND METHODS OF USE THEREOF

CROSS-REFERENCE TO RELATED APPLICATIONS

This application claims the benefit of U.S. Application Ser. No. 60/372,617, filed Apr. 11, 2002, the disclosure of which is incorporated herein by reference.

STATEMENT REGARDING FEDERALLY SPONSORED RESEARCH

This invention was made with government support under Grant Nos. AG-08200, AG-05138 and AG-17926 awarded by the National Institutes of Health. The government may have certain rights in the invention.

BACKGROUND OF THE INVENTION

Classic cadherins, including epithelial (E)- and neural (N)-cadherins, are major cell-cell adhesion receptors involved in the development, maintenance and function of most tissues, including the nervous system, epithelia and endothelia. In addition, cadherins play important roles in cell signaling, proliferation and differentiation. In cadherin-based adherens junctions (CAJ), the extracellular domains of transmembrane cadherins promote cell-cell adhesion by engaging in $Ca^{++}$-dependent homophilic interactions, while the cytoplasmic domains are linked to the actin cytoskeleton via α- and β-catenins. Post-translational regulation of cadherin adhesive activities, including proteolytic processing of cadherins and disassembly of CAJ, play crucial roles in rapid changes in cell adhesion, signaling and apoptosis, but the molecular mechanisms involved in cadherin processing and CAJ disassembly remain mostly unknown.

Presenilin-1 (PS1) is a polytopic transmembrane protein involved in most cases of early-onset familial Alzheimer's disease (FAD). Cellular PS1 is cleaved to yield an N-terminal (PS1/NTF) and a C-terminal (PS1/CTF) fragment. Following cleavage, the resultant PS1 fragments form a stable 1:1 heterodimer which binds to the cytoplasmic juxtamembrane region of E-cadherin (Baki et al., (2001) Proc. Natl. Acad. Sci. USA, 98:2381-2386). PS1 is found in the ER-Golgi system, but upon formation of cell-cell contacts PS1 concentrates at intercellular sites at the cell surface where it forms complexes with the CAJ. In addition to E-cadherin, PS1 forms complexes with N-cadherin and it has been localized at synaptic sites. Recently it was reported that PS1 regulates a γ-secretase cleavage of both APP and Notch receptor and stimulates Aβ-production (Herreman et al., (2000) Nat. Cell Biol. 2:461-2).

In the brain, PS1 forms complexes with N-cadherin (Georgakopoulos et al. (1999) Mol. Cell. 4: 893-902), a type I transmembrane protein and a member of the classic cadherin family of $Ca^{++}$-dependent cell adhesion factors (Gumbiner (1996) Cell 84: 345-357). Both proteins are expressed in neurons and have been found at the synapse (Georgakopoulos et al. (1999); Uchida et al. (1996) J. Cell. Biol. 135: 767-779). N-cadherin homophilic interactions are thought to play an important role in holding together pre- and post-synaptic membranes (Fannon and Colman (1996) Neuron 17: 423-434) and N-cadherin has been shown to undergo molecular changes in response to synaptic activity (Tanaka et al. (2000) Neuron 25: 93-107). Furthermore, N-cadherin promotes axonal outgrowth and regulates synaptogenesis and long term potentiation (LTP) (Goda (2002) Neuron 35: 1-3).

PS1 is important for the γ-secretase cleavages of the amyloid precursor protein (APP), which result in the production of the Aβ peptide of Alzheimer's disease (AD) (De Strooper et al. (1998) Nature 391: 387-390). In addition to the classic γ-secretase cleavages of APP defined by the C-terminus of various Aβ species, the PS1/γ-secretase system promotes the γ-secretase-like, or ε-cleavage (Weidemann et al. (2002) Biochemistry 41: 2825-2835) of several type I transmembrane proteins, including APP, Notch1 receptor, E-cadherin and CD44. Although this cleavage is also sensitive to γ-secretase inhibitors, it takes place further downstream from the amyloidogenic γ-secretase cleavages at a site closer to the membrane/cytoplasm interface than the γ-cleavages (De Strooper et al. (1999) Nature 398: 518-522). It has been discovered in accordance with the present invention that in certain cases, like E-cadherin (see FIG. 1), the ε-cleavage is greatly stimulated by calcium imbalance or apoptosis. The ε-cleavage results in the release of soluble cytosolic peptides containing the intracellular domains (ICDs) of the cleaved substrate proteins. Some of these peptides have been shown to migrate to the nucleus where they may act as regulators of gene expression (for reviews see Ebinu and Yankner (2002) Neuron 34: 499-502; Fortini (2002) Nat Rev. Mol. Cell. Biol. 3: 673-684).

Transcriptional coactivator CBP (CREB binding protein) interacts with and regulates the activities of a multitude of signal-responsive transcription factors and may thus integrate converging gene-regulatory pathways (Goodman and Smolik (2000) Genes Dev. 14: 1553-1577). CBP acts as a scaffold that facilitates recruitment of additional transcriptional modulators on the basal transcriptional complex. In addition, CBP has an intrinsic histone acetyltransferase (HAT) activity that may be used to regulate transcription by acetylating chromatin (Bannister and Kouzarides (1996) Nature 384: 641-643). CBP regulates many physiological processes including cell growth, differentiation, and apoptosis. Changes in CBP activities are associated with a large number of developmental, neurodegenerative and mental retardation conditions, including the human Rubenstein-Taybi syndrome, and overexpression of Drosophila CPB can lead to neurodegeneration suggesting that cellular levels of CBP are tightly regulated. CBP is a coactivator of transcription factor CREB (cyclic AMP response element binding protein) that regulates the expression of a variety of genes that contain CREs (cyclic AMP response elements) in their promoters. CREB is implicated in a number of cellular processes and diseases (Mayr and Montminy (2001) Nat. Rev. Mol. Cell. Biol. 2: 599-609) and CREB-dependent gene expression is critical for the function and plasticity of the nervous system (Lonze and Ginty (2002) Neuron 35: 605-523) including long-term memory and learning in both vertebrates and invertebrates (Kandel (2001) Science 294: 1030-1038). Stimulation of CREB-mediated transcription requires phosphorylation at CREB-Ser133, an event that leads to the recruitment of CBP and stimulation of transcription (Chrivia et al. (1993) Nature 365: 855-859).

In accordance with the present invention it has been discovered that apoptosis or $Ca^{++}$ influx stimulates a PS1/γ-secretase-like cleavage of E-cadherin. It has been further discovered that PS1 binding to E-cadherin is required for PS1/γ-secretase-like cleavage of E-cadherin. This cleavage results in the release of the cytoplasmic sequence of E-cadherin, β-catenin and α-catenin to the soluble cytosol, thus facilitating disassembly of cadherin-based adherens junctions. It has further been discovered that peptides based upon the PS1 binding site of cadherin inhibit γ-secretase activity, and are thus useful for inhibiting amyloid formation. In addition, it has been discovered that PS1 promotes a γ-secretase-like, or ε-cleavage of N-cadherin. This cleavage results in the production of a soluble intracellular domain (ICD) fragment termed N-Cad/CTF2. This peptide fragment binds CBP and sequesters it to the cytoplasm thus decreasing nuclear CBP and suppressing CREB-mediated transcription.

BRIEF SUMMARY OF THE INVENTION

The present invention is directed to peptides and polypeptides that comprise the presenilin-1 (PS1) binding site of cadherin and functional equivalents thereof. In a preferred embodiment, the polypeptide comprises the cytoplasmic domain of cadherin or a fragment thereof capable of binding to PS1. In another preferred embodiment, the peptide or polypeptide comprises the sequence EGGGE (SEQ ID NO: 5). Compositions comprising the peptides or polypeptides are also provided.

In another embodiment, the invention is directed to a method of inhibiting PS1-mediated γ-secretase activity comprising contacting a cell capable of exhibiting such activity with a peptide or polypeptide comprising the PS1-binding site of cadherin or a functional equivalent thereof.

In another embodiment, the present invention provides a method of preventing or inhibiting amyloid deposition comprising administering to a subject in need of such treatment a composition comprising a peptide or polypeptide comprising the PS1-binding site of cadherin or a functional equivalent thereof.

The present invention is also directed to peptides and polypeptides that comprise the matrix metalloproteinase (MMP) cleavage site of cadherin and functional equivalents thereof, and compositions comprising such peptides or polypeptides. A method of inhibiting metastasis comprising administering a composition comprising such a peptide or polypeptide is also provided.

In another embodiment, the present invention provides a method of determining susceptibility to Alzheimer's disease. A method of identifying agents that modify PS1/γ-secretase-like processing of cadherin is also provided.

In another embodiment, the present invention provides a method of treating FAD comprising administering to a subject in need of such treatment a composition comprising an agent that increases levels of Cad/CTF2. Compositions comprising Cad/CTF2 are also provided.

DETAILED DESCRIPTION OF THE INVENTION

Figure 1:
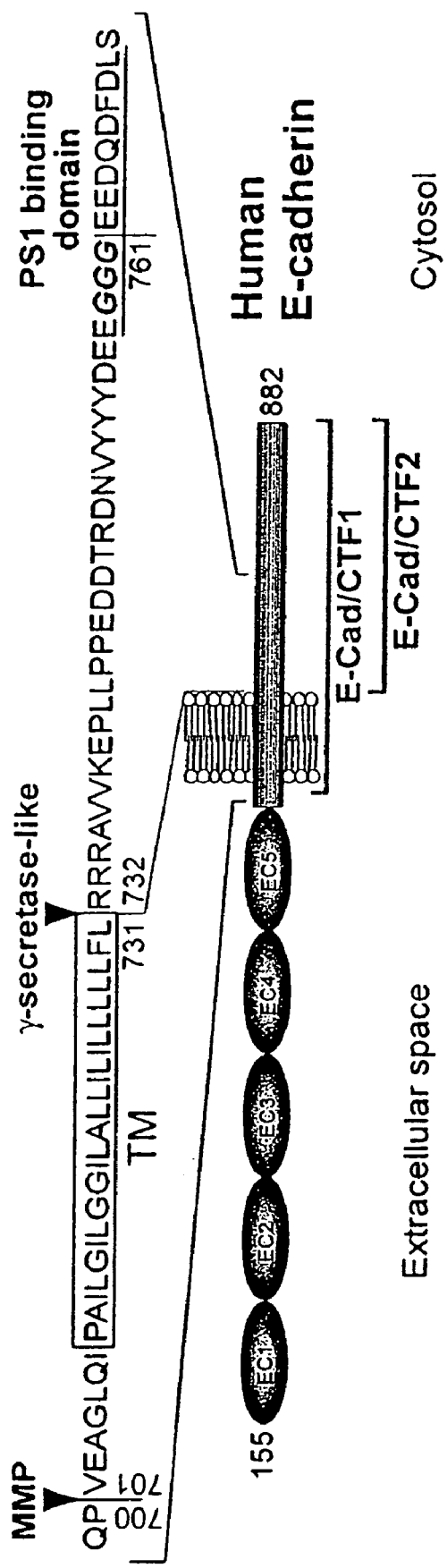
FIG. 1 is a diagram depicting a portion of the amino acid sequence of human E-cadherin (SWISS-PROT ACCESSION NO. P12830) (SEQ ID NO:19) indicating the N-termini of E-Cad/CTF1 and E-Cad/CTF2. Arrows identify the cleavage sites of MMP and PS1/γ-secretase-like cleavage. The sequence mediating E-cadherin-PS1 binding identified by Baki et al. (2001) Proc. Natl. Acad. Sci. USA 98:2381-2386 is underlined. EC1-5 denote the extracellular E-cadherin repeats. TM denotes the transmembrane domain.

In accordance with the present invention, it has been discovered that binding of PS 1 to the cytoplasmic domain of E-cadherin is required for processing of E-cadherin by the PS1/γ-secretase system. Further, it has been discovered that N-cadherin and VE-cadherin are also metabolized by the PS1/γ-secretase system. PS1 is involved in the processing of other cell surface transmembrane proteins including APP. By inhibiting the binding of PS1 to its substrate, proteolytic processing of the substrate is prevented. The present invention provides polypeptides and peptides that inhibit the binding of PS1 to its substrate, and thereby prevent proteolytic processing. Since the processing of APP is correlated with amyloid formation, the present peptides and polypeptides are useful in inhibiting amyloid formation and in the treatment and prevention of disorders characterized by amyloid formation.

In one embodiment, the present invention provides peptides and polypeptides that comprise the PS1 binding site of cadherin. The term cadherin, as used herein, includes epithelial (E-), neural (N-), vascular endothelial (VE-), and other homologous cadherins. The cadherin is preferably a mammalian cadherin, and more preferably a human cadherin. Cadherins and the amino acid sequences thereof are known in the art. As used herein, references to cadherin sequences are based upon the numbering of the unprocessed cadherin precursor. Amino acid sequences of cadherins are available in publicly accessible databases. For example, the amino acid sequence of human VE-cadherin is available at SWISS-PROT accession No. P33151. The amino acid sequence of human N-cadherin is available at SWISS-PROT accession No. P19022. The amino acid sequence of E-cadherin is available at SWISS-PROT accession No. P12830.

A polypeptide comprising the cytoplasmic domain of cadherin may be, for example, a polypeptide comprising amino acids 621-784 of VE-cadherin (P33151), a polypeptide comprising amino acids 647-906 of N-cadherin (P19022), or a polypeptide comprising amino acids 732-882 of E-cadherin (P12830). Those of ordinary skill in the art can identify polypeptides comprising the cytoplasmic domains of other cadherins. Fragments of these polypeptides that are capable of binding PS1 are also encompassed by the present invention. For example, a domain comprising amino acids 758-769 of E-cadherin is capable of binding PS1 as disclosed by Baki et al. (2001) Proc. Natl. Acad. Sci. USA 98:2381-2386, the disclosure of which is incorporated herein by reference. A preferred peptide of the present invention has the sequence EGGGEEDQDFDL (SEQ ID NO.: 1). A homologous peptide derived from the sequence of VE-cadherin has the sequence EGGGEMDTTSYD (SEQ. ID NO.: 2). A homologous peptide derived from the sequence of N-cadherin has the sequence EGGGEEDQDYDLS (SEQ. ID NO. 3). Those of ordinary skill in the art can determine other peptides capable of binding to PS1 by examining sequence similarities in other cadherins, or by conducting PS1 binding assays, or by performing deletion analysis as taught by Baki et al. In a preferred embodiment, the polypeptide or peptide comprises the sequence EGGGEED (SEQ. ID. NO.: 4). In another preferred embodiment, the polypeptide or peptide comprises the sequence EGGGE (SEQ. ID. NO.: 5).

Functional equivalents of the foregoing polypeptides and peptides are also provided by the present invention. Functional equivalents are defined herein as variants that maintain the ability to bind to PS1, including substitutions, insertions, deletions, additional sequences such as targeting sequences, tags, labeled residues, sequences to increase half-life or stability, or residues for any other purpose so long as the peptide maintains the ability to bind to PS1. The amino acids may be naturally occurring or modified, and may be L-amino acids or D-amino acids. The polypeptides and peptides of the invention may be modified, for example, by acylation or amidation. Peptide backbones may be modified, for example by substituted amide linkages.

The term functional equivalents also includes mimetics of the peptides and polypeptides of the present invention. Peptide mimetics are known to those of ordinary skill in the art and include peptides or non-peptide small molecules that have the activity of the peptide or polypeptide on which they are modeled. The design of such mimetics is based upon structure function studies of the peptides and polypeptides of the invention. Methods of determining protein structure are known in the art and include approximation by analogy to related proteins and other techniques including X-ray crystallography and computer modeling studies. These studies are used to design molecules that mimic the shape and function of the template peptide or polypeptides, which can then be synthesized by methods known in the art.

The peptides of the present invention are preferably from about six to about fifteen amino acids in length, and more preferably from about ten to about thirteen amino acids in length. Peptides may be modified to increase cell permeability, for example by linking the peptides to cell permeant peptide vectors such as Antennapedia (43-58), Arg/Trp analogue, TAT (48-60) and kFGF hydrophobic signal peptide region as described by Dunican et al. (2001) Biopolymers 60:45-60.

The peptides and polypeptides of the present invention may be synthesized by methods known in the art. Peptides may be synthesized, for example, by solid-phase methodology on an automated peptide synthesizer. Peptides may also be prepared by use of a combinatorial peptide library by methods known in the art. Polypeptides and peptides may also be prepared by recombinant methods, for example, by preparing expression vectors containing DNA encoding the desired polypeptide or peptide, transforming host cells with the vectors, culturing host cells under conditions whereby the polypeptide or peptide is expressed, and recovering the recombinant product.

The present invention further provides compositions comprising the PS1-binding peptides and polypeptides or functional equivalents thereof. The peptide, polypeptide or functional equivalent thereof may be in the form of a pharmaceutically acceptable salt. The compositions comprise one or more peptides or polypeptides or functional equivalents including mimetics as described above and may further comprise a carrier or diluent including for example solvents, dispersion media, antibacterial and antifungal agents, microcapsules, liposomes, cationic lipid carriers, isotonic and absorption delaying agents and the like.

In another embodiment, the present invention provides a method of inhibiting PS1-mediated γ-secretase activity comprising contacting a cell capable of exhibiting such activity with a composition comprising a peptide or polypeptide comprising the PS1-binding site of cadherin or a functional equivalent thereof.

PS1-mediated γ-secretase processing of APP is correlated with amyloid formation, and thus inhibition of PS1-mediated γ-secretase activity is useful for preventing or inhibiting amyloidosis, and thereby treating or preventing Alzheimer's disease. The invention provides a method of preventing or inhibiting amyloid deposition comprising administering to a subject in need of such treatment a composition comprising a peptide or polypeptide comprising the PS1-binding site of cadherin or functional equivalents thereof, in an amount effective to prevent or inhibit amyloid deposition.

The present invention further provides peptides and polypeptides that comprise the MMP cleavage site of cadherin and functional equivalents thereof. In accordance with the present invention, it has been discovered that the MMP cleavage site of human E-cadherin is at residues 700-101, i.e., seven residues to the extracellular side of the transmembrane domain of E-cadherin. This cleavage site is closer to the extracytoplasmic face of the plasma membrane than previously reported by Ito et al. (1999) Oncogene 18:7080-7090.

Peptides that comprise the MMP binding site of cadherin include peptides derived from the extracellular domain of cadherins adjacent to the transmembrane domain. Such peptides may comprise the sequences CEGAAQVCRKAQPVEAGLQI (SEQ. ID. NO.: 6) derived from E-cadherin; CDSNGDCTDVDRIVGAGLGTG (SEQ. ID. NO.: 7) derived from N-cadherin; and KCNEQGEFT-FCEDMAAQVGVS (SEQ. ID. No.: 8) derived from VE-cadherin, and the corresponding regions of other cadherins. In a preferred embodiment, the peptide comprises the sequence KAQPVEAGLQI (SEQ. ID. NO.: 9). In another preferred embodiment the peptide comprises the sequence QPVEA (SEQ. ID. NO.: 10). Fragments of these peptides and functional equivalents are also included. Functional equivalents are defined herein as variants that are capable of inhibiting cleavage of cadherin by MMP, and include the variants and modifications described hereinabove for the PS1-binding peptides and polypeptides, as well as mimetics as described hereinabove. The ability of the peptides and polypeptides to inhibit cleavage of cadherin can be assessed by contacting cultured cells with the peptide or polypeptide and assaying for cadherin cleavage, for example by immunoassays using antibodies against the MMP cleavage products of cadherin. The peptides may be synthesized as described hereinabove. The peptides are preferably from about six to fifteen, and more preferably from about ten to thirteen amino acids in length.

The present invention provides compositions that comprise peptides that comprise the MMP cleavage site of cadherin and functional equivalents thereof, such as mimetics. The compositions may further comprise a carrier or diluent as described hereinabove.

In tumor metastasis, inhibition of cadherin-mediated cell adhesion is promoted by cleavage of cadherin by MMP. The present polypeptides and peptides block cleavage of cadherin by MMP, and thus are useful in inhibiting metastasis. Accordingly, in another embodiment, the present invention provides a method of inhibiting tumor metastasis comprising administering to a subject in need of such treatment a composition comprising a polypeptide or peptide comprising the MMP cleavage site of cadherin or a functional equivalent thereof, in an amount effective to inhibit tumor metastasis. Inhibition of tumor metastasis can be assessed by those of ordinary skill in the art, for example, by conventional imaging methods.

Further, processing of cadherin by MMP results in CAJ disassembly, leading to apoptosis. The present polypeptides and peptides block this processing and thereby inhibit apoptosis. Accordingly, the present invention further provides a method of inhibiting apoptosis comprising contacting cells undergoing apoptosis with a composition comprising a polypeptide or peptide comprising the MMP cleavage site of cadherin or a functional equivalent thereof in an amount effective to inhibit apoptosis.

The polypeptides or peptides or their functional equivalents may be administered in a composition further comprising a pharmaceutically acceptable carrier. The formation of pharmaceutical compositions is known in the art and disclosed for example in Remington's Pharmaceutical Sciences, 17th edition, Mack Publishing Co., Easton, Pa. Polypeptide and peptide modifications as described above, for example peptides linked to cell permeant vectors, are particularly preferred for pharmaceutical compositions. The polypeptides, peptides or their functional equivalents may also be delivered by methods of gene therapy known in the art. Nucleic acids encoding the peptide or polypeptide are inserted into vectors such as genetically engineered adenovirus, adenoassociated virus, or herpes virus vectors, and the vectors are delivered to the subject in the form of a pharmaceutical composition. Nucleic acids encoding the peptides, polypeptides or functional equivalents may also be delivered by non-viral gene transfer systems such as liposome-DNA complexes or receptor-mediated gene transfer.

The effective amount of the peptide, polypeptide or functional equivalent to be used in the methods of the invention can be determined by the skilled artisan with consideration of individual differences in age, weight, extent of disease and condition of patient. The pharmaceutical forms containing the active agents may be administered in any convenient manner, either orally or parenterally, such as by intravenous, intraperitoneal, subcutaneous, rectal, implant, transdermal, slow release, intrabuccal, intracerebral or intranasal administration. Generally, the active agents need to pass the blood brain barrier and may have to be chemically modified, e.g. made hydrophobic, or linked to cell permeant vectors to facilitate this or be administered directly to the brain or via other suitable routes. For injectable use, sterile aqueous solutions are generally used or alternatively sterile powders for the extemporaneous preparation of sterile injectable solutions may be used. The solutions must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The prevention of the action of microorganisms can be brought about by various antibacterial and antifungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active agents in the required amount in the appropriate solvent with various of the other ingredients enumerated above, as required, followed by sterilization by, for example, filtration or irradiation. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active agents are suitably protected they may be orally administered, for example, with an inert diluent or with an assimilable edible carrier, or may be enclosed in hard or soft shell gelatin capsule, or may be compressed into tablets, or may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like.

As disclosed hereinabove, the PS1/γ-secretase system promotes classic γ-secretase cleavages of APP defined by the C-terminus of various Aβ species. In addition, it promotes a γ-secretase-like cleavage of several transmembrane proteins, including cadherin. The γ-secretase-like cleavage takes place further downstream from the amyloidogenic γ-secretase cleavages, at a site closer to the membrane/cytoplasm interfaces than the γ-cleavages. The γ-secretase-like cleavage is also designated ε-cleavage, and those terms are used interchangeably herein.

The γ-secretase-like cleavage, or ε-cleavage, results in the production of an intracellular domain (ICD) cleavage product. The ICD cleavage product is also referred to herein as Cad/CTF2 and the ε-cleavage product.

Certain mutations of PS1 are known to result in the development of a specific form of Alzheimer's disease known as Familial Alzheimer's disease (FAD). It has been reported that these mutations increase the production of amyloid-β. Hardy (1997) Trends Nerosci. 20:154-159. However, it has not heretofore been clear how these mutations cause FAD. In accordance with the present invention it has been discovered that PS1 mutants are impaired in their ability to mediate γ-secretase-like, or ε-cleavage of N-cadherin and other cadherins. This impairment results in reduced production of the N-cadherin ICD cleavage product (N-Cad/CTF2). The production of the C-terminal MMP cleavage product N-Cad/CTF1 is not impaired.

It has further been discovered in accordance with the present invention that the δ-cleavage product of N-cadherin (e.g. N-Cad/CTF2) binds transcription factor CBP (CREB binding protein) and sequesters CBP to the cytoplasm. Sequestration of CBP to the cytoplasm results in inhibition of CRE-dependent transactivation and inhibition of expression of CBP/CREB-regulated genes such as c-fos. It has also been discovered in accordance with the present invention that PS1 FAD mutations including M146L, A246E, E280A, ΔE9, G384A, E280G and Y115H inhibit N-Cad/CTF2 production and upregulate CREB-mediated transcription. The FAD mutation thus cause a gain of transcriptional function by inhibiting production of the transcriptional repressor N-Cad/CTF2.

Accordingly, the present invention provides a method of determining susceptibility to Alzheimer's disease comprising measuring the ICD product of the c-cleavage of cadherin in a cell, wherein a reduction in the cleavage product relative to the levels in control cells from normal individuals is indicative of susceptibility to Alzheimer's disease.

In a preferred embodiment, the ICD ε-cleavage product that is measured is N-Cad/CTF2 or E-Cad/CTF2 or VE-Cad/CTF2. E-Cad/CTF2, depicted in FIG. 1 (SEQ ID NO:19), comprises amino acids 732-882 of human E-cadherin (SWISS-PROT P12830). N-Cad/CTF2 comprises amino acids 747-906 of human N-cadherin (SWISS-PROT P19022). VE-Cad/CTF2 comprises amino acids 621-784 of VE-cadherin (SWISS-PROT P33151). The ICD cleavage products of other cadherins are defined as the C-terminal portion of cadherin generated by the γ-secretase-like ε-cleavage. The production of the ICD ε-cleavage product may be assessed in cells obtained from tissue of a patient, including non-neural tissue such as skin, or from cell cultures established from a patient.

Reduced levels of Cad/CTF2 may indicate that the patient has an FAD PS1 mutation and is therefore at risk of developing FAD. Alternatively, there may be reduced Cad/CTF2 in the absence of a FAD PS1 mutation indicating a risk of developing sporadic AD. Cad/CTF2 may be measured by conventional methods of protein detection. A detectable reduction in Cad/CTF2 relative to controls by such methods is sufficient for the present method. The measurement need not be quantitative. In a preferred embodiment, one of the many immunoassays well-known in the art is used to detect and qualitatively measure Cad/CTF2. Suitable assays include ELISA, Western blotting, and radioimmunoassay. For example, cell extracts may be probed by conventional Western blots using an anti-cytoplasmic N-cadherin or anti-cytoplasmic E-cadherin antibody or anti-cytoplasmic VE-cadherin antibody. Such an antibody will recognize both the Cad/CTF1 and Cad/CTF2 fragments, which are distinguishable on Western blots by their relative molecular weights, with the Cad/CTF2 fragment having a lesser molecular weight. Such antibodies may be obtained commercially (e.g. C36 from BD Transductor Laboratories) or raised by conventional methods known in the art, disclosed for example in Antibodies: A Laboratory Manual, Harlow et al., eds, Cold Spring Harbor Laboratories, 1988.

The present invention further provides a method for identifying agents that modify PS1/γ-secretase-like processing of cadherin. Such agents are useful as candidate compounds for treatment of conditions implicated in cadherin processing, including for example Alzheimer's disease. The method comprises contacting a cell containing cadherin with a test compound; measuring production of the ICD cleavage product of cadherin; and comparing production of the cleavage product in cells contacted with the test compound to production in cells not contacted with the test compound; wherein a difference in production of the cleavage product in the presence of the test compound is indicative of an agent that modifies γ-secretase-like processing of cadherin. In accordance with the present invention it has been found that the ionophore ionomycin modifies PS1/γ-secretase-like processing of cadherin and is thus a candidate compound for treatment of conditions implicated in cadherin processing.

The assay may be in vitro or in vivo. For example, the cell may be a cultured cell or a cell obtained from a mammal to which the test compound has been administered. Suitable cell lines include mammalian, preferably human cells such as HEK293, HeLa cells, primary human enthothelial cells, primary human fibroblasts or lymphoblasts, primary human mixed brain cells, Chinese hamster ovary cells, and the like.

The mammal may be, for example, a monkey, dog, rabbit, guinea pig, rat or mouse. In a preferred embodiment the mammal may be an animal model for Alzheimer's disease, such as a PS1 P264L homozygous knock-in mouse described by Siman et al. (2000) J. Neurosci. 20:8717-26. The compound may be administered in a composition and by a route of administration as described hereinabove.

In a preferred embodiment the cell is from a cultured human cell line. The cells may be cells that overproduce cadherin, for example as a result of transfection with cadherin cDNA. The cell may be a cell in which PS1 contains one or more mutations for example a cell transfected with a mutant PS1 known to be correlated with FAD.

Measurements of the γ-secretase-like cleavage product of cadherin, i.e. the soluble ICD fragment termed Cad/CTF2, may be accomplished by any technique capable of detecting Cad/CTF2. Immunological detection methods using binding substances for Cad/CTF2 such as antibodies and antibody fragments are preferred. Suitable detection methods include ELISA, Western blotting and radioimmunoassay. As discussed hereinabove, antibodies that recognize Cad/CTF2 cross-react with Cad/CTF1, and thus Western blotting or other methods that permit separation of Cad/CTF2 and Cad/CTF1 are preferred.

The test compound may be any agent that can be added to the cell without substantially interfering with cell viability, including for example small molecules, polymers including polypeptides, polysaccharides, polynucleotides and the like, and may be natural or synthetic, and may be a single substance or a mixture, for example a cell extract. Ionophores, and in particular calcium ionophores such as ionomycin and A23187, are specifically contemplated. Also contemplated are agonists of ionotropic receptors, such as the N-methyl-D-aspartate (NMDA) receptor. Such agonists include NMDA, 1-aminocyclobutane-1,3-dicarboxylic acid, aspartic acid, 2-carboxy-3-carboxy methylquinoline, cysteinesulphinic acid, glutamic acid, homoquinolinic acid, "-amino-(3-hydroxy-5-isoxazolyl)acetic acid and tetrazol-5-yl-glycine.

In another embodiment, the present invention provides a method of identifying agents that modify CREB-mediated transcription. Such agents are useful as candidate compounds for treatment of conditions implicated in unregulated CREB-mediated transcription, such as FAD. The method comprises contacting a cell capable of undergoing CREB-mediated transcription with a test compound; measuring CREB-mediated transcription, and comparing CREB-mediated transcription in cells contacted with the test compound to CREB-mediated transcription in cells not contacted with the test compound; wherein a difference in CREB-mediated transcription in the presence of the test compound is indicative of an agent that modifies CREB-mediated transcription.

The assay may be performed in vitro or in vivo, using cells, mammals and test compounds as described above. A detectable difference in CREB-mediated transcription relative to controls is sufficient for the present method.

CREB-mediated transcription may be measured by using cells transfected with a reporter gene under the control of a promoter containing a CRE, and measuring expression of the reporter gene. CREB-mediated transcription may also be assessed by measuring expression of genes known to be regulated by CREB, e.g. c-fos. A change in the amount of c-fos mRNA or c-fos protein in the absence of an effect on transcription of genes that are not regulated by CREB, e.g. gadph or β-tubulin, is indicative of the identification of an agent that modifies CREB-mediated transcription. The mRNA and protein levels may be measured by methods known in the art, such as semiquantitative RT-PCR and Western blotting. Test compounds that modify CREB-mediated transcription include ionophores, NMDA receptor agonists, and Cad/CTF2.

The present invention further provides agents that modify CREB-mediated transcription. In a preferred embodiment, the agent binds to CBP and sequesters CBP to the cytoplasm. In a preferred embodiment the agent is the ICD cleavage product of cadherin. In another preferred embodiment the agent is N-Cad/CTF2, E-Cad/CTF2 or VE-Cad/CTF2. Such agents can be produced as described hereinabove, e.g. by standard methods of recombinant technology, or obtained as cleavage products isolated from the naturally occurring mammalian proteins. Compositions comprising the agents are also provided, and may be formulated as described hereinabove.

The present invention further provides a method for treating FAD characterized by decreased Cad/CTF2 production. The method comprises administering to a subject in need of such treatment a composition comprising an agent that increases levels of Cad/CTF2 in the subject. In another embodiment, the method comprises administering an agent that decreases CREB-mediated transcription in a subject. In a preferred embodiment, the subject exhibits a PS1 FAD mutation associated with decreased N-Cad/CTF2 production and upregulated CREB-mediated transcription as characterized hereinabove. The agent may be, e.g., Cad/CTF2 itself or functional equivalents thereof that maintain the ability to bind CBP and sequester it to the cytoplasm. Functional equivalents are defined hereinabove. In a preferred embodiment the agent is N-Cad/CTF2. The agent may also be PS1, or functional equivalents as defined above that maintain the ability to cleave cadherin and produce Cad/CTF2. The agent may also be an agent that stimulates PS1 ε-cleavage activity, such as an NMDA receptor agonist or other agent defined by the assay described above. The agents may be modified to increase cell permeability as described above. Compositions may be formulated and administered as described hereinabove.

All references cited herein are incorporated herein in their entirety.

The following examples serve to further illustrate the present invention.

Example 1

Materials and Methods

The following materials and methods were used in examples 2-7.

Materials and antibodies. GM6001 was obtained from Chemicon International, Inc., Staurosporine was from Sigma, Ionomycin and Z-DEVD-FMK were from Calbiochem. L-685,458 and its inactive analogue were kindly provided by Dr. M. S. Shearman (Merck Research Labs). Rabbit polylonal antibody R222 was raised against amino acids 2-12 of human PS1/NTF and mouse monoclonal antibody 33B10 is specific for residues 331-350 of human PS1/CTF (Georgakopoulos et al., (1999) Mol. Cell. 4:893-902. Rabbit polyclonal antibody R1 was raised against human APP751 amino acids 729-751 (Anderson et al., (1989) Embo. J. 8:3627-3632). Anti-E-cadherin (clone C36), anti-β-catenin and anti-α-catenin monoclonal antibodies were obtained from BD Transduction Laboratories; antibody H108 against E-cadherin ectodomain was obtained from Santa Cruz Biotechnology, Inc.

Mouse embryo preparation. Wild-type and PS1 knock-out mouse embryos (Baki et al., (2001) Proc Natl. Acad. Sci. USA 98:2381-2386) were collected at day 18.5 post coitum and solubilized by mechanical dissociation and sonication in RIPA buffer (50 mM Tris-HCl [pH 8], 150 mM NaCl, 0.1% SDS, 1% Nonidet P40, 0.5% sodium deoxycholate, 1× Complete protease inhibitor cocktail, Roche). Fifty micrograms of extract was analyzed by Western blotting.

Cell Cultures and transfections. Cells were grown in Dulbecco's Modified Eagle Medium (DMEM) plus 10% fetal bovine serum, penicillin and streptomycin in 5% $CO_2$ at 37° C. Fibroblast cell lines derived either from wild-type (WT) (PS1+/+) or PS1 knock-out (PS1−/−) mice were stably transfected with human E-cadherin as described by Baki et al., (2001). A431 cells were from American Type Culture Collection. Stable transfectants of PS1 cDNA in HEK293 cells were prepared as described by Georgakopoulos et al., (1999). A431D cells stably transfected with wild-type or GGG759-761AAA mutant E-cadherin were provided by Dr. A. B. Reynolds.

Subcellular fractionation. Confluent A431 cells (one 100 mm dish) were rinsed and scraped with 4° C. phosphate-buffered saline (PBS). Cells were then placed into 1 ml of buffer A (20 mM Tris-HCl [pH 7.5], 0.25 M sucrose, 10 mM EGTA, 2 mM EDTA, 1× Complete protease inhibitor cocktail, Roche), passed through a 27 gauge needle 10 times, and the obtained cell lysate was centrifuged at 500×g for 10 min at 4° C. The supernatant was then centrifuged at 120,000×g for 45 min at 4° C. to separate the cytosolic and crude membrane fractions. The pellet (crude membrane fraction) was washed twice with buffer A and resuspended by sonication in 400 ml of buffer A containing 1% Triton X-100. The suspension was incubated at 4° C. for 30 min and then centrifuged at 120,000×g for 45 min at 4° C. to separate the membrane and Triton X-100-insoluble fractions. The pellet (Triton X-100-insoluble fraction) was washed twice with buffer A and solubilized by sonication in RIPA buffer. 20 mg of proteins from the different fraction were analyzed by SDS-PAGE.

Immunoprecipitations (IPs), immunoblotting, immunofluorescence and confocal microscopy. For WB analysis of cell extracts, cells were washed with PBS and then solubilized in RIPA buffer. For IPs cells were solubilized in Hepes buffer (25 mM Hepes [pH 7.4], 150 mM NaCl, 1× Complete protease inhibitor cocktail, Roche) containing 1% digitonin (IPs with I-R222 and PI-R222 antibodies) or 1% Triton X-100 (IPs with β-catenin and desmoglein antibodies). Following centrifugation at 17,000×g for 10 min, supernatants (1 mg protein) were pre-cleared with protein A- or protein G-agarose (Pierce) for 2 hours. Supernatants were then incubated with antibodies overnight at 4° C. and treated for 2 hours with protein A-agarose (polyclonal antibodies) or with protein G-agarose (monoclonal antibodies). IPs were washed with Hepes buffer containing either 1% digitonin or 1% Triton X-100 and analyzed by SDS-PAGE. Immunofluorescence and confocal microscopy was performed as described by Georgakopoulos et al., (1999). Briefly, cells were plated on 22×22 mm collagen-coated glass coverslips, fixed in cold methanol for 10 min at −20° C. Following washing in TBS (25 mM Tris-HCl [pH 7.4], 150 mM NaCl), cells were treated with 10% goat serum in SuperBlock (Pierce) for 1 hour, incubated overnight with primary antibody (1:100), washed in TBS and then were incubated with species specific Alexa Fluor™ secondary antibody conjugates (Molecular Probes). Cells were washed with TBS, mounted with Prolong antifade kit (Molecular Probes), and photographed on a Leica confocal laser scanning microscope.

Purification, mass spectrometry, and amino-terminal sequence analyses of E-cadherin carboxyl-terminal fragments. A431 cells treated with 1 mM of staurosporine for 6 hours were solubilized by sonication in RIPA buffer. 50 mg of protein extract were pre-cleared with 20 mg of H108 antibody, 20 mg of unrelated monoclonal antibody and a mixture of protein A- and protein G-agarose (Pierce). The pre-cleared supernatant was treated overnight with 120 mg of C36 anti-E-cadherin antibody and immunoglobulins were precipitated with 500 ml of protein G-agarose. Immunoprecipitates were split in two samples and submitted to SDS-PAGE. One sample was stained with GelCode blue stain reagent (Pierce) and the 33 kDa and 38 kDa fragments of E-cadherin were submitted to MALDI-MS Peptide Mass Mapping after in-gel digestion (Dr. M. A. Gawinowicz, HHMI/Columbia University Protein Core Facility). The second sample was transferred on to a polyvinylidene difluoride (PVDF) membrane and the 38 kDa and 33 kDa bands corresponding to E-Cad/CTF1 and E-Cad/CTF2 respectively, were subjected to sequential derivitization and cleavage of N-terminal amino acids by Edman chemistry followed by reverse phase HPLC chromatography (automated Applied Biosystems Procise 492 Peptide Sequencer, New York University Protein Analysis Facility).

Example 2

A PS1/γ-Secretase-Like Activity Controls E-Cadherin Processing

Extracts from PS1-knock-out mouse embryos (PS1−/−) were used to investigate whether PS1 plays any role in E-cadherin processing. Extracts from PS1+/+ or PS1−/− mouse embryos were probed on Western blots with either anti-cytoplasmic E-cadherin C36 or anti-cytoplasmic APP R1 antibodies. PS1−/− embryos had significantly higher amounts of a 38 kDa peptide that contained the cytoplasmic sequence of E-cadherin (E-Cad/CTF1) than did wild-type (WT, PS1+/+) embryos even though all embryos had similar levels of the full-length E-cadherin. PS1−/− embryos also contained increased levels of APP α-stubs.

Extracts from E-cadherin-transfected PS1+/+ or PS1−/− mouse fibroblasts were probed with anti-E-cadherin C36 or 33B10 antibodies. E-Cad/CTF1 accumulated in the fibrobast cell line that was derived from PS1−/− mice compared to the cell line from PS1+/+mice, even though both cell lines expressed comparable amounts of transfected full-length E-cadherin. The accumulation of E-Cad/CTF 1 in PS1−/− cells under conditions of constant levels of the full length protein indicated that a PS1-mediated activity controls metabolism of E-Cad/CTF1.

PS1+/+fibroblasts were treated for 6 hours either with the γ-secretase inhibitor L-685,458 (0.5 μM) or with dimethylsulfoxide. Extracts from these cell cultures were then probed with anti-E-cadherin C36. Treatment of the E-cadherin-transfected PS1+/+ fibroblasts with the selective γ-secretase inhibitor L-685,458 increased cellular E-Cad/CTF1 compared to non-treated controls, indicating that the PS1-associated γ-secretase activity is involved in the metabolism of E-Cad/CTF1.

Although the foregoing data indicated that peptide E-Cad/CTF1 is further processed by a PS1/γ-secretase cleavage, E-cadherin metabolites resulting from this activity either in embryos or in PS1+/+ fibroblasts were not detected. The apparent molecular weight and immunoreactivity of E-Cad/CTF1, however, suggested that this fragment derives from a matrix metalloproteinase (MMP) cleavage of the E-cadherin ectodomain. Since this cleavage is stimulated by apoptosis (Steinhusen et al., (2001) J. Biol. Chem. 276:4976-4980), the levels of the PS1/γ-secretase cleavage product of E-cadherin in apoptotic conditions was investigated. Human epithelial cell line A431 that expresses high levels of endogenous E-cadherin and undergoes apoptotis under staurosporine treatment (STS)(Steinhusen et al., (2001)) was used as a model. A431 cells were treated for 1, 2, 3, 4, 5 or 6 hours with 1 μM of STS to induce apoptosis, solubilized in RIPA and blotted with anti-E-cadherin C36 antibody. STS treatment of this cell line resulted in a time-dependent production of three E-cadherin carboxy-terminal fragments migrating at 38, 33, and 29 kDa respectively.

A431 cells were also preincubated for 30 minutes in the absence or presence of GM6001 (2.5 μM), Z-DEVD-FMK (50 μM), an inactive analogue of L-685,458 (0.5 μM), or L-685,458 (0.5 μM). Cells were then treated with STS for 6 hours to induce apoptosis, and cell extracts were probed with C36 antibody. Production of the 38 kDa fragment was inhibited by the MMP inhibitor GM60001 (Galardy et al., (1994) Ann. N.Y. Acad. Sci. 732:315-323) indicating that this fragment which has identical immunoreactivity and apparent molecular mass as E-Cad/CTF1 is derived from a MMP cleavage of E-cadherin.

Conditional media (20 μl) from A431 cells cultured in the absence or presence of GM60001 and treated with SDS as above were probed on Western blots with anti-E-cadherin ectodomain antibody H108. STS increased a secreted 95 kDa fragment detected with the E-cadherin ectodomain antibody H108. This fragment (termed E-Cad/NTF1), does not react with antibodies against cytoplasmic E-cadherin and, like E-Cad/CTF1, it is also inhibited by GM60001 suggesting that E-Cad/NTF1 is the secreted counterpart of E-Cad/CTF1. The 29 kDa fragment (E-Cad/CTT3) is inhibited by the specific caspase-3 inhibitor Z-DEVD-FMK indicating it is produced by an apoptosis-stimulated caspase-3 cleavage of E-cadherin (Steinhusen et al., (2001).

The γ-secretase inhibitor L-685,458 completely blocked production of the 33 kDa cadherin fragment (E-Cad/CTF2) indicating that this fragment is produced by a γ-secretase-like cleavage of E-cadherin. Inhibition of E-Cad/CTF2 by L-685, 458 correlates with an increase in E-Cad/CTF1 indicating that the former peptide derives from the later by a γ-secretase-like activity.

Extracts of HEK293 cells stably transfected with PS1 or vector alone were immunoprecipitated and probed with C36 antibody or anti-PS1/NTF antibody R222. Over-expression of PS1 in cell line HEK293 increased E-Cad/CTF2 and decreased E-Cad/CTF1. That E-Cad/CTF2 is produced even when E-Cad/CTF1 is inhibited indicates that the PS1/γ-secretase-dependent E-Cad/CTF2 can also be derived from full-length E-cadherin.

A431 cells were pre-incubated for 30 minutes in the absence or presence of GM6001 (1.5 μM). Cells were then treated with STS for 6 hours and cell extracts were probed on Western blots with H108 or C36 antibodies. A 100 kDa E-cadherin fragment recognized by antibody H108 but not by anti-cytoplasmic E-cadherin antibody C36 was detected in cell extracts of GM60001-treated A431 cultures, indicating that this fragment (E-Cad/NTF2) is the N-terminal counterpart of E-Cad/CTF2. In addition to A431 and HEK293 cells, two other cell lines, SW480 and LNCaP, also produced the PS1/γ-secretase fragment E-Cad/CTF2 under Ca++ influx conditions indicating that this is a general mechanism of E-cadherin processing.

Example 3

Identification of the PS1/γ-Secretase and MMP-Mediated Cleavage Sites of E-Cadherin E-Cad/CTF 1 and E-Cad/CTF2 were affinity purified from STS-treated A431 cells. Antibody H108 against E-cadherin sequence 600-707 (numbering according to the full length unprocessed human E-cadherin) reacted with secreted E-Cad/NTF1 but not with cellular E-Cad/CTF1 indicating that the MMP cleavage of E-cadherin occurs closer to the extracytoplasmic face of the plasma membrane than previously reported by Ito et al., (1999) Oncogene 18:7080-7090. Indeed, Edman sequencing of E-Cad/CTF1 through 14 cycles showed the following major sequence: VEAGLQIPAILGIL (SEQ. ID NO.: 11). This is a unique sequence corresponding to human E-cadherin residues 701-714. The N-terminus of this sequence is located seven residues upstream of the transmembrane sequence of E-cadherin. Mass spectrometry analysis of E-Cad/CTF1 showed no peptides upstream of the cleavage site that was determined by Edman sequencing. Thus, the 38 kDa E-Cad/CTF1 is produced by a MMP cleavage after E-cadherin residue Pro$^{700}$. Edman sequencing of E-Cad/CTF2 yielded the following sequence: RRRAVVKEPLL (SEQ. ID. NO.: 12). This is a unique sequence corresponding to human E-cadherin residues 732-742. Mass spectrometric analysis of E-Cad/CTF2 yielded E-cadherin peptides predicted from the sequencing data. These results show that the PS1-mediated γ-secretase cleavage of E-cadherin takes place between residues Leu$^{731}$ and Arg$^{732}$ at the interface of the membrane with the cytoplasm. The foregoing results are summarized schematically in FIG. 1. The indicated γ-secretase-like cleavage is also called the E-cleavage that produces Cad/CTF2 fragments.

Example 4

The γ-Secretase-Mediated Cleavage of E-Cadherin Promotes Disassembly of Adherens Junctions The molecular weight and immunoreactivity of the isolated peptides suggest that they contain the entire E-cadherin cytoplasmic sequence including the β-catenin binding site (Steinberg et al., (1999) Curr. Opin. Cell. Biol. 11:554-560). Extracts from STS-treated A431 cells were immunoprecipitated with antibodies against PS1 (I-R222), pre-immune serum (PI-R222), β-catenin or desmoglein, and the immunoprecipitates obtained were probed on Western blots with anti-E-cadherin antibody C36. These co-immunoprecipitation experiments showed that the MMP cleavage product E-Cad/CTF1 binds both β-catenin and PS1 whereas the γ-secretase product E-Cad/CTF2 binds only β-catenin. Thus, the PS1/γ-secretase-like cleavage of E-cadherin dissociates PS1 from the E-cadherin/β-catenin complex.

A431 cells treated for 6 hours with STS were fractionated into membrane, soluble cytosolic and Triton X-100-insoluble fractions, and the fractions were probed on Western blots with C36 antibody. This subcellular fractionation of STS-treated A431 cells showed that full-length E-cadherin and E-Cad/CTF1 are found only in the membrane and cytoskeletal (Triton X-100-insoluble) fractions while E-Cad/CTF2 localizes in the membrane and in the soluble cytosol indicating that the PS1/-γ-secretase-like cleavage results in the solubilization of the cytoplasmic sequence of E-cadherin. In stable cell-cell adhesion, the E-cadherin/β-catenin complex of the CAJ is anchored to the actin cytoskeleton via catenin and this association is manifested by the insolubility of the complex components in Triton X-100 (Baki et al., (2001)). Induction of apoptosis or calcium influx disrupts cadherin-mediated cell-cell adhesion by cleaving cadherin and disassembling the CAJ complexes. To determine whether the γ-secretase cleavage of E-cadherin is involved in the CAJ disassembly, calcium influx was induced with ionomycin (10 μM) in A431 cells preincubated for 30 minutes in the absence or presence of the γ-secretase inhibitor L-685,458. Cell extracts were fractionated, and analyzed on Western blots with antibodies against cytoplasmic E-cadherin C36 or β- and α-catenins. In the absence of this inhibitor, ionomycin induced a time-dependent decrease in the cytoskeletal (Triton X-100-insoluble) fraction of both full-length E-cadherin and E-Cad/CTF1 and this decrease correlated with a corresponding increase in soluble cytosolic E-Cad/CTF2. Similarly, ionomycin decreased the cytoskeletal association (Triton X-100-insoluble fraction) of the CAJ components β-catenin and α-catenin with a concomitant significant increase in their soluble cytosolic levels. These data indicate that ionomycin induces a time-dependent disassembly of the E-cadherin/catenin cytoskeletal complex resulting in increased production of the PS1/γ-secretase fragment E-Cad/CTF2 and in the solubilization of cytoskeletal β- and α-catenins. L-685,458 blocked the ionomycin-induced metabolism of cytoskeletal E-Cad/CTF1 and partially inhibited degradation of the full length E-cadherin while it abolished production of soluble cytosolic E-Cad/CTF2, suggesting that L-685,458 inhibits the γ-secretase-like cleavage of both cytoskeletal full-length E-cadherin and E-Cad/CTF1. In addition, L-685,458 delayed the ionomycin-induced decrease of cytoskeletal β-catenin and α-catenin and inhibited their release to the soluble cytosol. These data show that the γ-secretase-like ε-cleavage of E-cadherin promotes dissociation of the CAJ components from the cytoskeleton and their release to the soluble cytosol.

The PS1/γ-secretase role in the disassembly of CAJ was further examined using laser scanning confocal microscopy (LSCM). A431 cells were pre-incubated for 30 minutes in the absence or presence of L-685,458 and then treated for 45 minutes with ionomycin. Following the ionomycin-induced cell-cell dissociation, the distribution of PS1, E-cadherin, β-catenin and α-catenin was analyzed by LSCM using the constant detector setting. Cells were double-labeled with either anti-PS2/NTF antibody R222 and anti-cytoplasmic E-cadherin antibody C36, or with anti-ectodomain E-cadherin antibody H108 and anti-β-catenin antibody. Cells were also labeled for α-catenin. PS1, cytoplasmic and ectodomain sequences of E-cadherin, β-catenin and α-catenin concentrated at cell-cell contacts in confluent A431 cells. Ionomycin treatment disrupted cell-cell adhesion and decreased plasma membrane staining of all epitopes. PS1, cytoplasmic E-cadherin, β-catenin and α-catenin staining became more diffuse throughout the cytoplasm. In contrast, cadherin ectodomain staining was barely detectable suggesting a significant reduction of the cellular levels of this epitope in agreement with the ionomycin-induced cleavage and secretion of E-cadherin ectodomain.

Pre-incubation with L-685,458 significantly delayed loss of cell surface staining of all epitopes. Ectodomain E-cadherin staining was also partially preserved at the cell surface and at cell-cell contacts in agreement with the foregoing data that L-685,458 inhibits the ionomycin-induced metabolism of cytoskeletal full-length E-cadherin. However, two-color immunofluorescence of L-685,458-treated cells revealed a cell population containing β-catenin but no ectodomain E-cadherin at the cell surface suggesting that these represent junctional complexes of β-catenin with E-Cad/CTF1. In L-685,458-treated cultures, there was a complete junctional overlap between staining of cyoplasmic E-cadherin and PS1 suggesting that cell surface PS1 remains bound to both full-length E-cadherin and E-Cad/CTF1. This observation concurs with the foregoing biochemical data showing that PS1 binds both full-length E-cadherin and E-Cad/CTF1.

Example 5

A Cadherin Mutant Unable to Bind PS1 is not Cleaved by the PS1/γ-Secretase Activity To examine whether PS1 binding to E-cadherin is necessary for the PS1/γsecretase cleavage, E-cadherin mutant GGG759-761AAA was used (Thoreson et al., (2000) J. Cell Biol. 148:189-202). E-cadherin-negative A431D cells were stably transfected either with WT E-cadherin or with the E-cadherin mutant. Extracts from the transfected cells were immunoprecipitated with anti-PS1/NTF antibody R222, and the immunoprecipitates were probed with anti-E-cadherin antibody C36 or anti-PS1/CTF antibody 33B10. In contrast to WT protein, mutant E-cadherin failed to bind PS1 consistent with reports that E-cadherin sequence 760-771 (corresponding to 604-615 residues of mature processed E-cadherin) is necessary for PS1/E-cadherin binding (Baki et al., (2001)).

A431D cells stably transfected with WT E-cadherin or with the E-cadherin mutant were incubated in the absence or presence of ionomycin for 45 minutes and RIPA extracts were probed on Western blots with C36 antibody. Cytosolic fractions were probed with antibodies against E-cadherin (C36), β-catenin or α-catenin. Upon ionomycin treatment, cells expressing WT E-cadherin showed a significant increase in soluble E-Cad/CTF2, β-catenin and α-catenin. In contrast, cells expressing mutant E-cadherin showed no ionomycin-induced increase in soluble β- or α-catenin. Furthermore, no soluble E-Cad/CTF2 was detected in mutant transfectants either in the presence or absence of ionomycin. Thus, PS1 binding to E-cadherin is required for the PS1/γ-secretase cleavage of E-cadherin and for the release of E-Cad/CTF2, β-catenin and α-catenin to the soluble cytosol.

Example 6

Overexpression of E-Cadherin Reduces Amyloid-β Production

Figure 2:
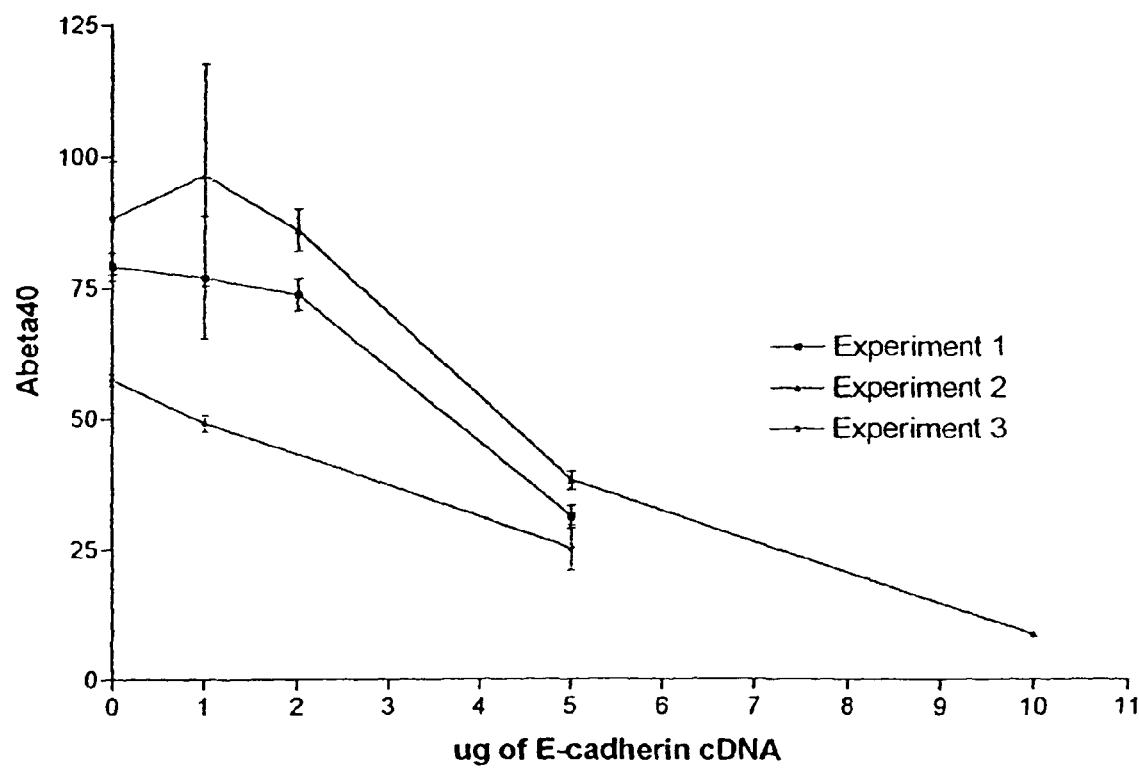
FIG. 2 is a dose-response graph demonstrating that the production of amyloid-β (1-40) decreases with increasing expression of E-cadherin.
Figure 3:
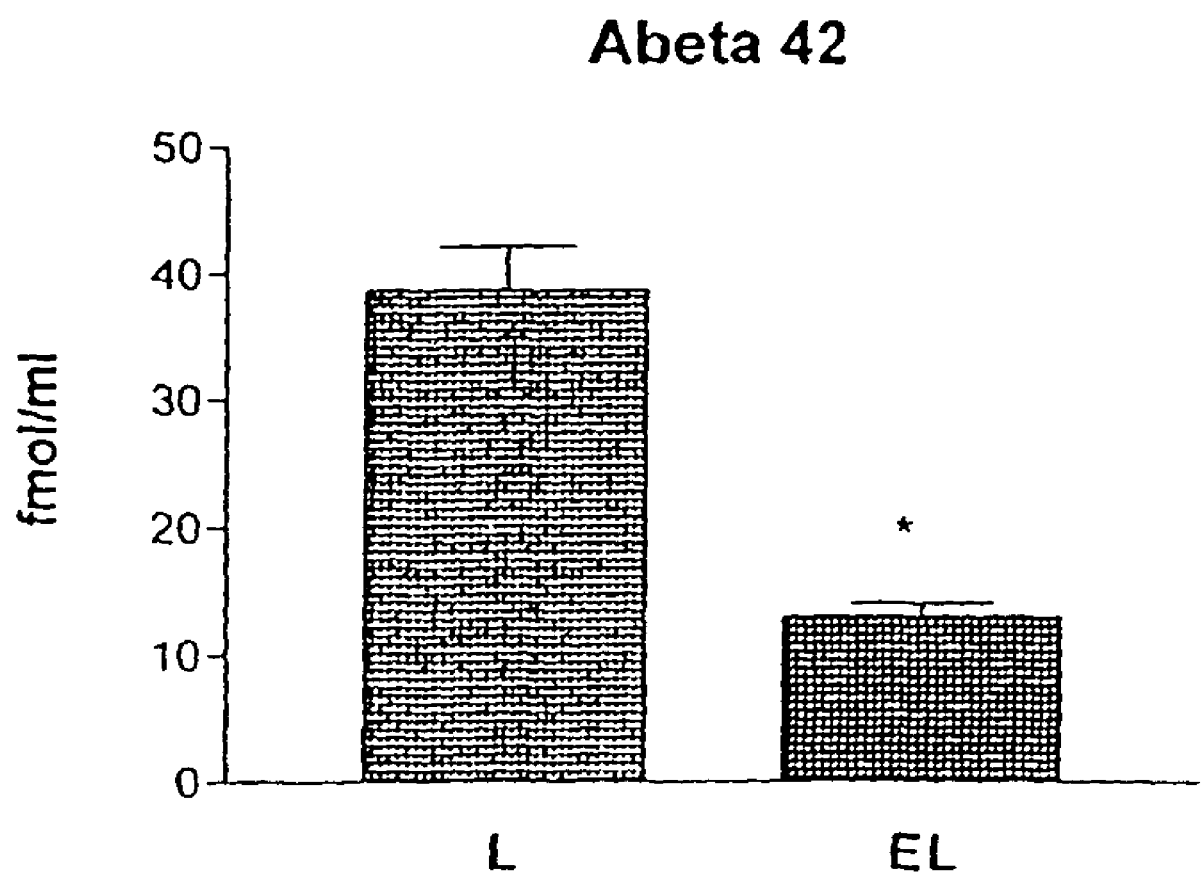
FIG. 3 is a bar graph depicting the production of amyloid-β (1-42) in cultures of control (L) and E-cadherin-transfected (EL) cells.
Figure 4A:
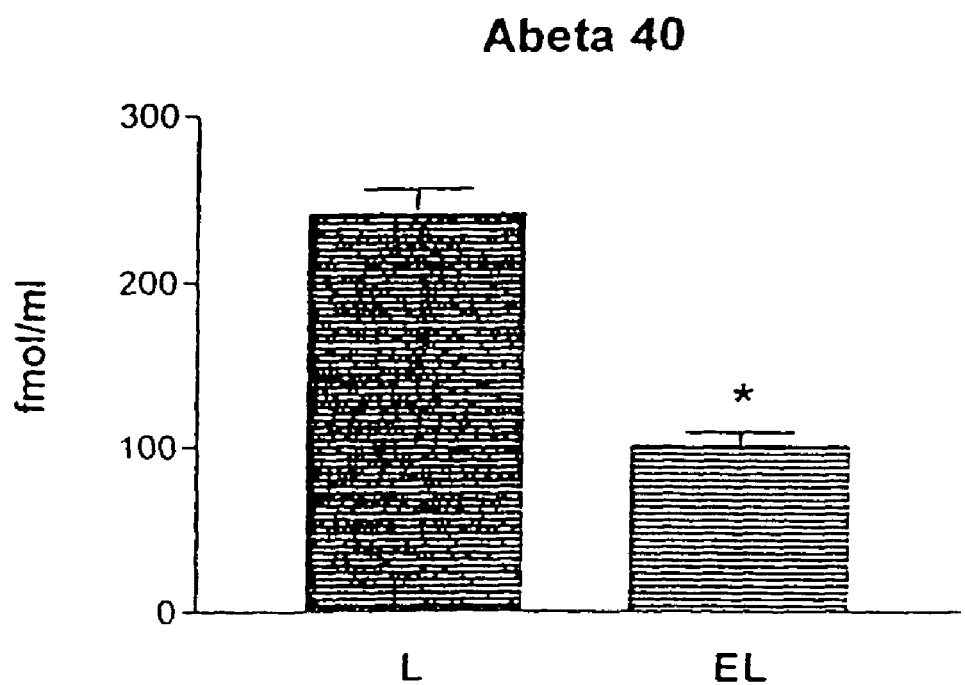
FIG. 4A is a bar graph depicting the production of amyloid-β (1-40) in cultures of control (L) and E-cadherin-transfected (EL) cells.

L cell cultures were transfected with increasing amounts of human E-cadherin. Amyloid-β (1-40) and amyloid-β (142) were measured by ELISA. FIG. 2 is a dose-response graph demonstrating that the production of amyloid-β (1-40) decreases with increasing expression of E-cadherin. FIG. 3 is a bar graph depicting the production of amyloid-β (1-42) in cultures of control (L) and E-cadherin-transfected (EL) cells. FIG. 4A is a bar graph depicting the production of amyloid-β (1-40) in cultures of control (L) and E-cadherin-transfected (EL) cells. These results demonstrate that overexpression of E-cadherin significantly reduces amyloid-β production.

Figure 4B:
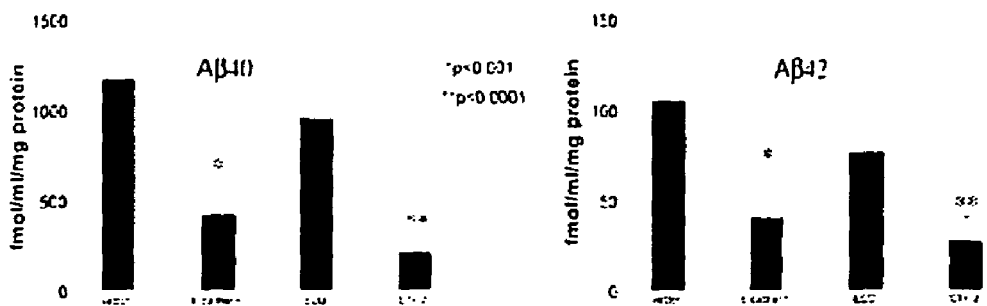
FIG. 4B is a bar graph demonstrating that cytoplasmic E-cadherin (E-Cad/CTF-2) inhibits Aβ$_{40}$ and Aβ$_{42}$ in CHO cells expressing Swedish APP mutant

CHO cells expressing Swedish APP mutant were transiently transfected with vector cDNA (vector), full length E-cadherin (E-cadherin), a cDNA construct encoding the transmembrane and ectodomain sequence of E-cadherin (EC0) or a cDNA expressing the entire cytoplasmic sequence of E-cadherin (CTF2). Secreted $A\beta_{40}$ and $A\beta_{42}$ were determined by ELISA. Results are shown in FIG. 4B. Each value is a mean±SD from three assays each performed in duplicate. Expression of E-cadherin and CTF-2 but not EC0 significantly inhibited $A\beta_{40}$ and $A\beta_{42}$ (*$p<0.001$, **$p<0.0001$, t test), suggesting that cytoplasmic sequences of E-cadherin are implicated in the inhibition of Aβ. Expression of transfected proteins in swCHO cells was monitored by Western blotting.

Example 7

FAD-PS1 Mutations Inhibit the γ-Secretase-Like ε-Cleavage of N-Cadherin

Figure 5A:
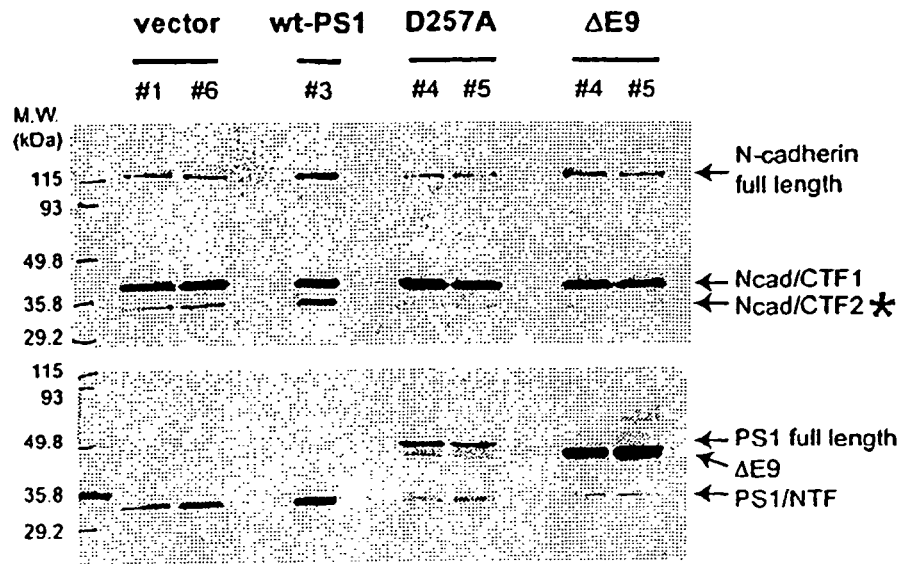
FIG. 5 is a Western blot depicting cadherin and cadherin cleavage products in cells transfected with wild-type and mutant PS1.
Figure 5B:
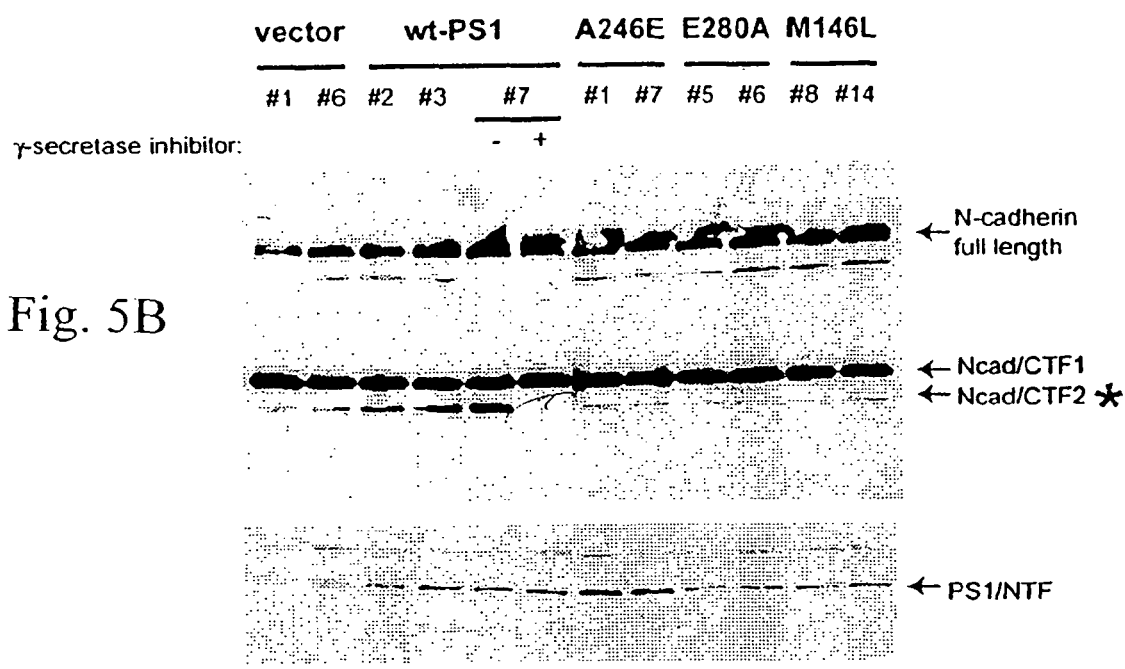

HEK293 cells were stably transfected with wild-type or mutant (D2574A, ΔE9, A246E, E280A or M146L) PS1. Membrane preparations were incubated and then analyzed by Western blots with either anti-cytoplasmic N-cadherin (FIGS. 5A and B, upper panels) or anti-PS1/N-terminal fragment (PS1/NTF) (FIGS. 5A and B, lower panels) antibodies. The results are shown in FIGS. 5A and 5B. Ncad/CTF1 and Ncad/CTF2 indicate C-terminal fragments of N-cadherin. Ncad/CTF1 is produced by a metalloproteinase activity, while Ncad/CTF2 is an ε-cleavage product. In the lanes numbered 7 in FIG. 5B, the cell line overexpressing wild-type PS1 was incubated in the absence (−) or presence (+) of the selective γ-secretase inhibitor, L-685,458.

As demonstrated in FIGS. 5A and 5B, compared to cells transfected with wild-type PS1, the production of Ncad/CTF2 was inhibited in cells transfected with the PS1 mutants, and in cells transfected with wild-type PS1 and incubated with a γ-secretase inhibitor. Production of Ncad/CTF1 was comparable in cells transfected by wild-type and mutant PS1. These results demonstrate that PS1 mutations inhibit the γ-secretase-like processing of N-cadherin.

Figure 6:
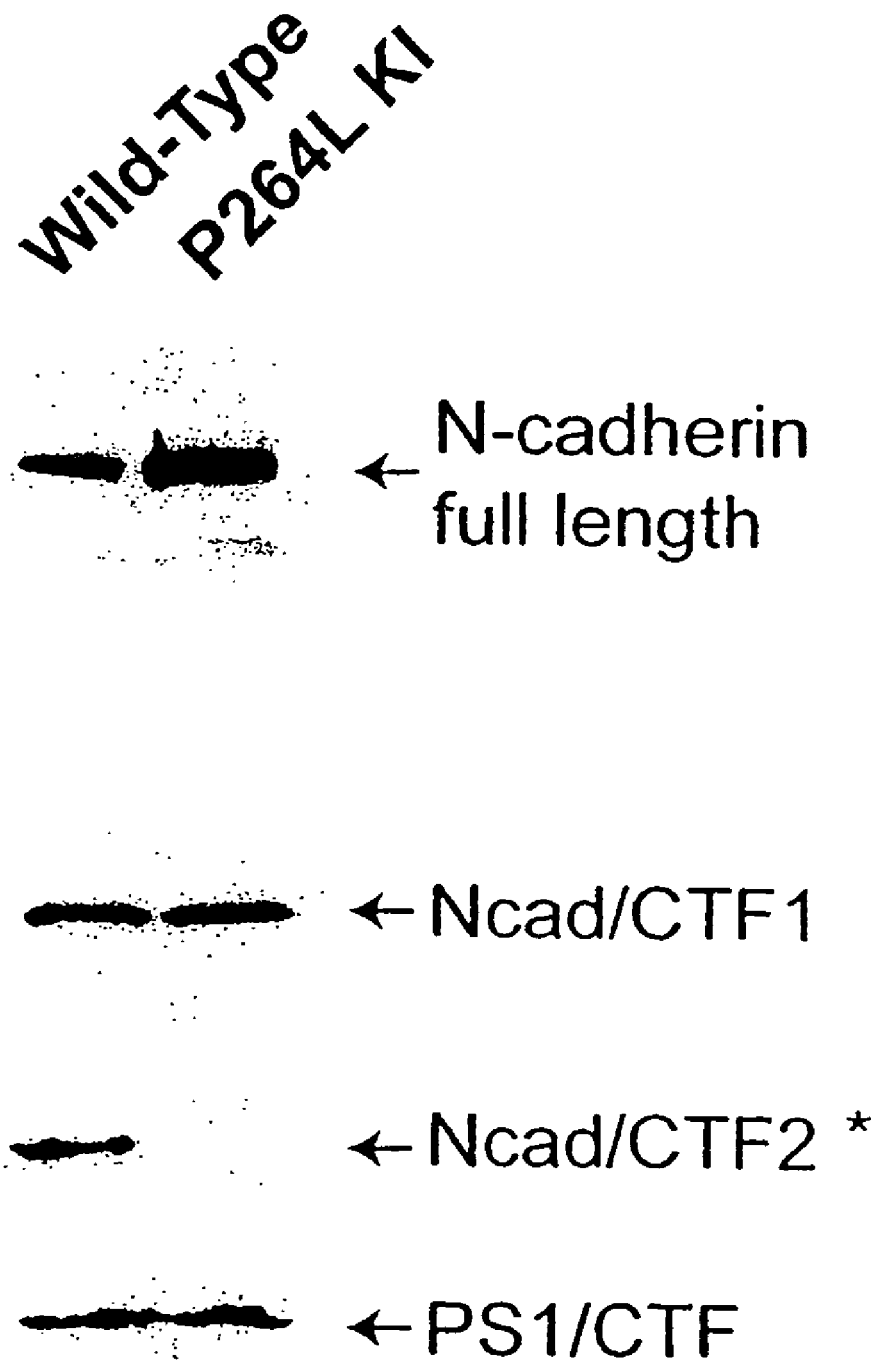
FIG. 6 is a Western blot depicting N-cadherin and N-cadherin cleavage products in fibroblasts from PS1 wild-type and PS1 P264L homozygous knock-in mice.

Membrane preparations were obtained from embryonic fibroblasts of PS1 wild-type and PS1 P264L homozygous knock-in mice Siman et al. (2000) J. Neurosci. 20:8717-26. The preparations were analyzed by Western blots with either anti-cytoplasmic N-cadherin (FIG. 6, upper three panels) or anti-PS1/C-terminal fragment (FIG. 6, lower panel) antibodies. As demonstrated in FIG. 6, ε-cleavage of N-cadherin was inhibited in the PS1 P264L knock-in mouse fibroblasts, but not in fibroblasts from PS1 wild-type mice. Production of the metalloproteinase cleavage product, Ncad/CTF1, was not affected.

Example 8

Materials and Methods

The following materials and methods were used in the subsequent examples.

Materials and antibodies. L-685,458 was obtained from Calbiochem, GM6001 from Chemicon, D(−)-2-amino-5-phosphonovalerate (D-APV), L-Glutamate and N-methyl-D-aspartic acid (NMDA) were from Sigma. Rabbit polyclonal antiserum R222 against PS1/NTF residues 2-12 and mouse monoclonal antibody 33B10 specific for PS1/CTF residues 331-350 were prepared as described by Georgakopoulos et al. (1999) Mo. Cell 4: 893-902. Anti-N-cadherin (clone C32) and anti-E-cadherin (C36) monoclonal antibodies were obtained from BD Transduction Laboratories. Anti-b-tubulin, anti-CBP (A-22) and anti-c-fos polyclonal antibodies were from Santa Cruz Biotechnology. Antibodies against phosphorylated CREB at Ser133 (1B6) was from Cell Signaling Technology.

Cell lines, cell culture and transfections. N2a, HEK293, L cells were grown in Dulbecco's Modified Eagle's Medium (DMEM) plus 10% fetal bovine serum, penicillin and streptomycin in 5% $CO_2$ at 37° C. Embryonic fibroblasts from PS1 P264L-homozygous knock-in mice were prepared as described by Siman et al. (2001) J. Neurosci. 20: 8717-8726. HEK293 cell lines stably transfected either with WT or mutant PS1 cDNAs cloned into pC1-neo expression vector were grown in the presence of G418. L cells were transfected with chicken cytoplasmic domain of N-cadherin (N-Cad/CTF2) inserted into vector pECE (pN-Cad/CTF2) or with full length mouse CBP inserted into vector pRc/RSV.

Immunoprecipitations (IPs), immunoblotting and immunofluorescence. IPs were performed as described by Marambaud et al. (2002) EMBO J. 21: 1948-1956 in 4° C. HEPES buffer (25 mM HEPES, pH 7.4, 150 mM NaCl, 1× Complete protease inhibitor cocktail, Roche) containing 0.5% Nonidet P40 (NP40). For western blot (WB) analysis, cells were solubilized in 4° C. RIPA buffer (50 mM Tris-HCl, pH 8, 150 mM NaCl, 0.1% SDS, 1% NP-40, 0.5% sodium deoxycholate, 1× Complete protease inhibitor cocktail) as described by Marambaud et al. (2002). Immunofluorescence was performed as described by Georgakopoulos et al. (1999) with the following modifications: to visualize nuclei, cells were treated for 5 minutes with 4',6-diamidino-2-phenylndole (DAPI, 1:5000; Sigma). Fluorescence microscopy and digital image acquisition were carried out using an Axioskop2 microscope (Zeizz).

Mouse embryo preparation. Mouse PS1+/+, +/− or −/− embryos or mouse embryonic brains were collected at E18.5 and solubilized in RIPA buffer as described by Baki et al. (2001) Proc. Natl. Acad. Sci. USA 98: 2381-2386. Fifty micrograms of extract were analyzed on WBs.

Primary, neuronal cultures. Mixed hippocampal and cortical neuronal cultures were prepared from E18 mouse or rat brains as described by Banker and Goslin (1991) Culturing Nerves Cells, London, MIT Press. Neurons were maintained 10 days in vitro in glial conditioned MEM containing 2% glucose and N2 supplements as described by Bottenstein and Sato (1979) Proc. Natl. Acad. Sci. USA 76: 514-517, and then were stimulated for 15 minutes with Mg2+-free Hanks' balanced salt solution (HBSS, Sigma) containing KCl (50 mM), L-Glutamate (50 mM) or NMDA (50 mM). D-APV (100 mM) was applied 15 minutes before stimulation.

In vitro γ-secretase-like ε-cleavage assay. Cells were washed in PBS, resuspended in 1 ml of 4° C. hypotonic buffer (10 mM MOPS, pH 7.0, 10 mM KCl) and homogenized on ice. A post-nuclear supernatant was prepared by centrifugation at 1000×g for 15 minutes at 4° C. Crude membranes were isolated from the post-nuclear supernatant by centrifugation at 16,000×g for 40 minutes at 4° C. The membranes were then resuspended in 25 ml of assay buffer (150 mM sodium citrate, pH 6.4, 1× Complete protease inhibitor cocktail), and incubated at 37° C. for 2 hours. Samples were either analyzed directly by WB or separated into pellet (P100) and supernatant (S100) fractions by ultracentrifugation for 1 hour at 100,000×g at 4° C. The S100 and P100 fractions were then analyzed by WB.

Transactivation assays. CRE-dependent transactivation was measured in the absence or presence of overexpression of PKA (pFC-PKA, Stratagene) by cotransfection with CRE-luciferase reporter plasmid (pCRE-Luc, Stratagene) and pSV-β-galactosidase vector (Promega) to evaluate transfection efficiency. CHOP-mediated transactivation was measured by cotransfection with the Gal4-fusion trans-activator plasmids (pFA-CHOP and pFR-Luc, Stratagene). 30 hours after transfection, luciferase and β-galactosidase activities were determined following manufacturer's instructions using a TD-20/20 luminometer (Turner Designs) and a DU-64 spectrophotometer (Beckman). Values were normalized to β-galactosidase activity and protein concentration.

Subcellular fractionation. Transfected cells were washed in PBS, placed into 1 ml of buffer A (20 mM Tris-HCl, pH 7.5, 0.25 M sucrose, 10 mM EGTA, 2 mM EDTA, 1x Complete protease inhibitor cocktail), and then passed through a 27 gauge needle 10 times. Obtained lysates were centrifuged at 500×g for 10 minutes and pellets (nuclear fraction) were washed twice with 1 ml of buffer A containing 0.1% Triton X-100 and solubilized by sonication in RIPA buffer. Supernatants were centrifuged at 120,000×g for 45 minutes at 4° C. to separate cytosolic and crude membrane fractions. A 50 µg protein aliquot from the nuclear and cytosolic fractions was analyzed on WBs.

Reverse Transcriptase (RT)-PCR Analysis. Total RNA was extracted from cells using a RNeasy Mini Kit (Qiagen) according to instructions by the manufacturer. Analysis of gene expression was performed using semiquantitative RT-PCR. The following primers were used: 5'-GGGTTTCAACGCCGACTACG-3' (SEQ ID NO: 13) and 5'-CAGCTTGGGAAGGAGTCAGC-3' (SEQ ID NO: 14) for c-fos; 5'-TGTCGTGGAGTCTACTGG-3' (SEQ ID NO: 15) and 5'-CAGCATCAAAGGTGGAGG-3' (SEQ ID NO: 16) for gapdh.

Electrophoresis mobility shift assay (EMSA). Nuclear extract from CBP-transfected L cells were prepared using the extraction kit N-XTRACT (Sigma) according to manufacturer's instructions. Ten microgram of nuclear extract was used for EMSA performed according to manufacturer's instructions using biotinylated double-stranded oligonucleotide probes containing DNA-binding motifs for CREB or MEF-1 (Panomics). Probes are as follow: CREB, 5'-AGAGATTGC-CTGACGTCAGAGAGCTAG-3' (SEQ ID NO: 17); MEF-1, 5'-GATCCCCCCAACACCTGCTGCCTGA-3' (SEQ ID NO: 18). Reaction products were separated on 6% polyacrylamide gels in cold TBE buffer (50 mM Tris-HCl, 45 mM Boric acid, 0.5 mM EDTA), transferred to nylon membranes (Immobilon-Ny+, Millipore) and bound probes were immobilized for 30 minutes at 85° C. and visualized by chemiluminescence using streptavidin-HRP conjugate. For antibody supershift analysis, nuclear extract was incubated for 3 hours at 4° C. with 2 ml of 1 B6 antibody prior to probe addition. Where indicated, nuclear extract (20 mg) was immunoprecipitated with A-22 antibody (1 ml) and protein A-agarose in EBC buffer (50 mM Tris, pH 8, 120 mM NaCl, 0.5% NP40, 1× Complete protease inhibitor cocktail). Immunoprecipitates were washed twice with EBC buffer and twice with buffer B (20 mM HEPES, pH 7.5, 50 mM KCl, 10 mM MgCl2, 10% glycerol, 0.5 mM DTT). Immunoprecipitates were then eluted with 0.8% sodium deoxycholate in buffer B. The supernatants were made 1.2% NP40 and used for EMSA.

Example 9

PS1-Mediated γ-secretase-Like Activity Cleaves N-cadherin

Figure 7A:
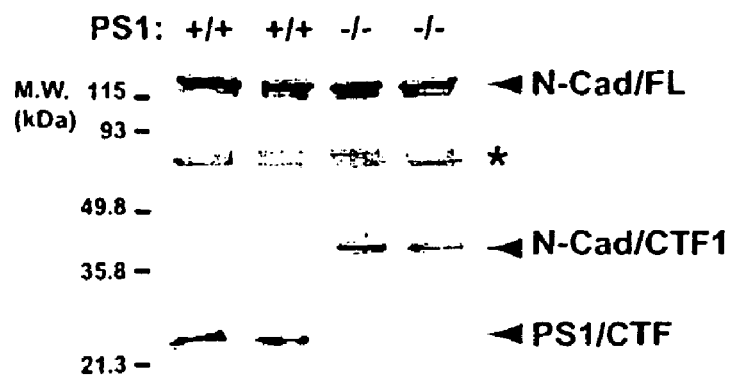
FIGS. 7A-D are Western blots depicting N-cadherin, N-cadherin cleavage products and PS 1 in extracts from PS1+/+ and PS1−/− embryos (FIG. 7A), PS1+/+ and PS1−/− fibroblasts (FIG. 7B), membranes from PS1+/+ and PS1−/− fibroblasts and N2a cell cultures (FIG. 7C) and membranes from HEK293 cells transfected with wild type PS1 and D257A-PS1.

Extracts from PS1+/+ or PS1−/− mouse embryos were probed on WBs with either anti-cytoplasmic N-cadherin antibody (FIG. 7A, upper panel) or anti-PS I/CTF antibody 33B10 (FIG. 7A, lower panel). Extracts from PS1+/+ or PS1−/− fibroblast cultures were incubated for 16 hours in the absence or presence of DMSO, L-685,458 (0.5 µM) and probed on WBs with either C32 or 33B10 antibodies.

Figure 7B:
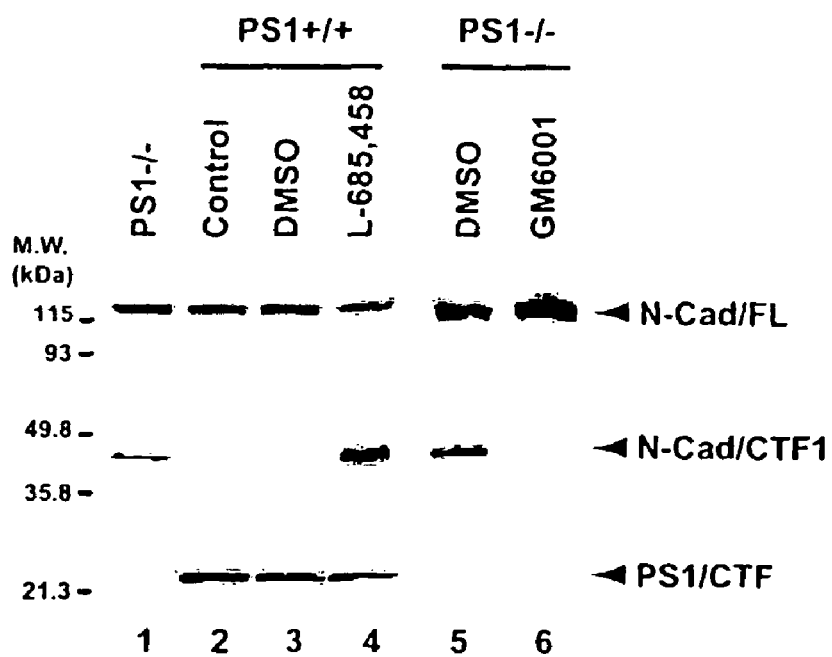

PS1 knockout (PS1−/−) mouse embryos accumulated a 40 kDa peptide (termed N-Cad/CTF1) detected with antibodies against the cytoplasmic sequence of N-cadherin. This peptide was hardly detectable in wild type (WT) mouse embryos although all embryos contained similar amounts of full length N-cadherin (FIG. 7A). A similar peptide accumulates in PS1−/− fibroblasts or in WT fibroblasts treated with the γ-secretase inhibitor L-685,458 (Li et al. (2000) Nature 405: 689-694,) but not in control WT fibroblasts. All cultures contained similar amounts of full length N-cadherin (FIG. 7B, lanes 1-4). Matrix metalloproteinase (MMP) inhibitor GM6001 decreased N-Cad/CTF1 and increased full length N-cadherin (FIG. 7B, lanes 5 and 6). Together, these data indicate that N-Cad/CTF1 derives from full length N-cadherin through a MMP cleavage and is subsequently processed by a PS1-dependent γ-secretase-like activity. The corresponding peptide derived through the MMP cleavage of E-cadherin, a protein highly homologous to N-cadherin, is demonstrated in Example 2 hereinabove.

To detect the product of the PS1-dependent cleavage of N-cadherin, an in vitro assay that uses incubation of membrane fractions to detect the ICD product of the E-cleavage of APP was used. (Gu et al. (2001) J. Biol. Chem. 276:35235-35238; McLendon et al. (2000) FASEB J. 14:2383-2386).

Membranes from PS1−/− (FIG. 7C, lane 1) or PS1+/+ (FIG. 7C, lanes 2-4) fibroblasts or from N2a cell cultures (FIG. 7C, lanes 5-6) incubated for 16 hours in the absence or presence of DMSO or L-685,458 (0.5 mM), were incubated at 37° C. for 2 hours, separated by centrifugation in a pellet (P100, FIG. 7C, upper panels) and a soluble (S100, FIG. 7C, lower panels) fractions and then probed on WBs with C32 antibody. Membranes from HEK293 cell cultures stably transfected with vector alone (FIG. 7D, lanes 1 and 2), WT-PS1 (FIG. 7D, lanes 3-5), or D257A-PS1 (FIG. 7D, lanes 6 and 7) were incubated at 37° C. for 2 hours and then probed with either C32 (FIG. 7D, upper panel), anti-PS1/NTF (FIG. 7D, middle panel) or anti-PS1/CTF (FIG. 7D, lower panel) antibodies. Membranes from WT-PS1-transfected clone #7 were incubated in the absence (−) or presence (+) of L-685, 458 (FIG. 7D, lanes 4 and 5).

Figure 7C:
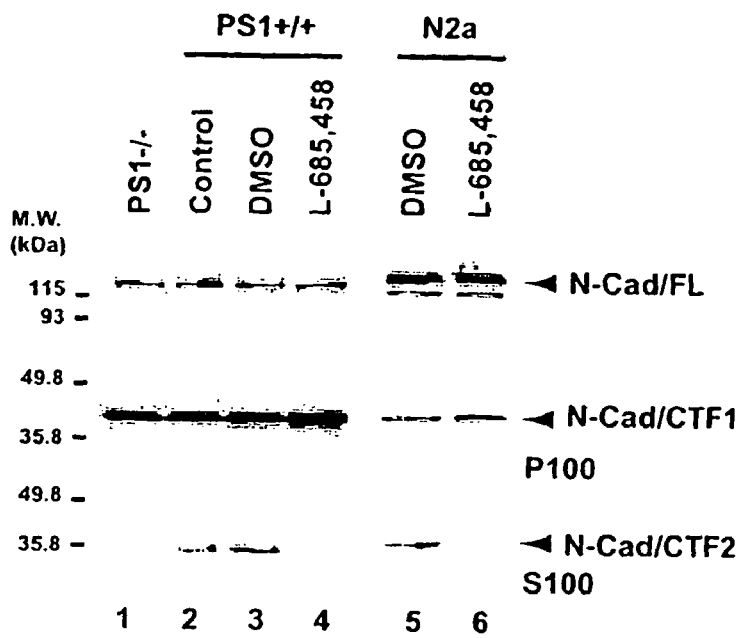
Figure 7D:
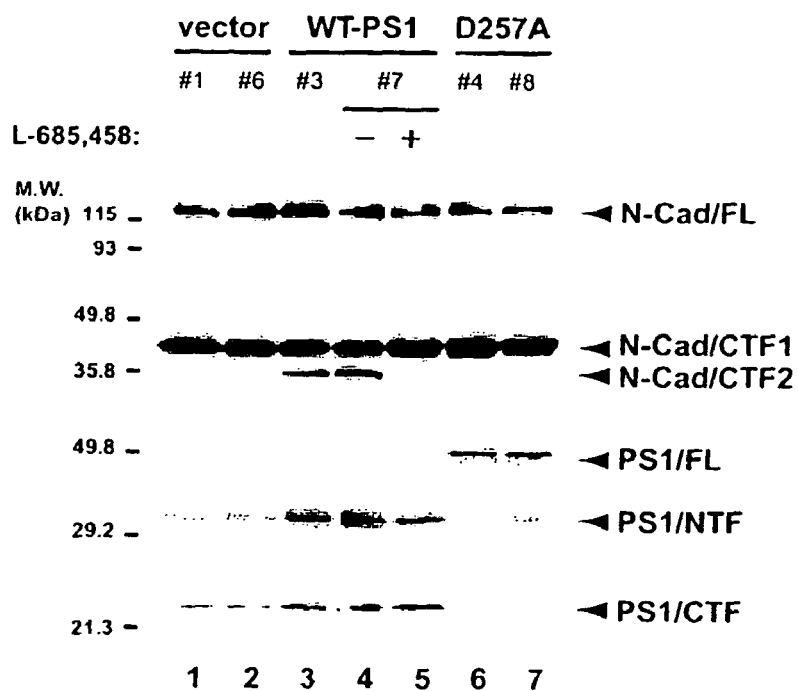

A soluble 35 kDa peptide, termed N-Cad/CTF2, containing the cytoplasmic sequence of N-cadherin was detected in this assay using membrane fractions from either mouse fibroblasts or from mouse neuroblastoma cell line N2a (FIG. 7C). N-Cad/CTF2 is greatly reduced in the absence of the PS1 gene and is completely absent from cultures treated with γ-secretase inhibitor L-685,458 (FIG. 7C). The residual N-Cad/CTF2 detected in PS1−/− cells is probably due to activity of PS2, a PS1 homologue (Levy-Lahad et al. (1995) Science 269:970-973; Rogaev et al. (1995) Nature 376:775-778). Overexpression of PS1 in HEK293 cells resulted in a significant stimulation of N-Cad/CTF2 production compared to membranes from vector-transfected cells (FIG. 7D, lanes 1-4). In contrast, no N-Cad/CTF2 was detected using membranes prepared either from cells overexpressing the γ-secretase dominant negative PS1 mutant D257A (Wolfe et al. (1999) Nature 398:513-517) (FIG. 7D, lanes 6 and 7) or from cells treated with γ-secretase inhibitor L-685,458 (FIG. 7D, lanes 4 and 5). Together with the apparent SDS-PAGE molecular mass of N-Cad/CTF2, these data indicate that N-cadherin undergoes a ε-cleavage by the PS1/γ-secretase system to release an ICD peptide of N-cadherin. Example 3 hereinabove shows that E-cadherin is processed by a similar mechanism to release E-Cad/CTF2.

Example 10

NMDA Receptor Agonists or Membrane Depolarization Stimulates the PS1/ε-Cleavage of N-Cadherin N-cadherin and PS1 are both expressed in neurons and in brain tissue they are found in the same complex (Georgakopoulos et al. (1999) Mol. Cell 4:893-902). N-cadherin is a synaptic component that undergoes structural changes following stimulation of the N-methyl-D-aspartate (NMDA) receptor (Tanaka et al. (2000) Neuron 25:93-107). PS1 has also been localized at the synapse (Georgakopoulos et al. (1999); Ribaut-Barassin et al. (2000) Synapse 35:96-110). To examine whether the PS1/γ-secretase system is involved in the processing of neuronal N-cadherin, membranes from a culture of primary neurons prepared from brains of WT and PS1−/− mouse embryos were tested. Membranes prepared from PS1−/− (FIG. 8A, lane 1) PS1+/+ (FIG. 8A, lane 2) or PS1+/− (FIG. 8A, lanes 3 and 4) mouse brain neuronal cultures were incubated at 37° C. for 2 hours. PS1+/− neurons were incubated in the absence (−) or presence (+) of L-685, 458 (0.5 µM). Following incubation samples were probed with C32 (FIG. 8A, upper panel) or R222 (FIG. 8A, lower panel).

Figure 8A:
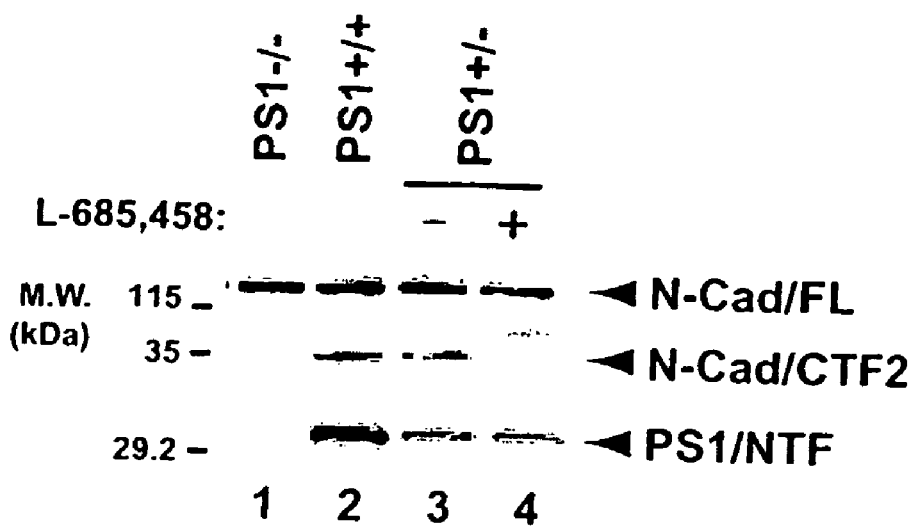
FIGS. 8A and B are Western blots depicting N-cadherin, N-cadherin cleavage products and PS1 in membranes of PS1+/+, PS1−/− and PS1+/− mouse brain neuronal cultures (FIG. 5A) and membranes of rat brain neurons preincubated in the absence or presence of D-APV and stimulated with KCl, L-glutamate or NMDA.

FIG. 8A (lanes 1 and 2) shows that N-cadherin ICD fragment N-Cad/CTF2 is detected in membranes from WT cultures but not in membranes from PS1−/− cultures. Furthermore, N-Cad/CTF2 peptide is inhibited by γ-secretase inhibitor L-685,458 (FIG. 8A, lanes 3 and 4).

Figure 8B:
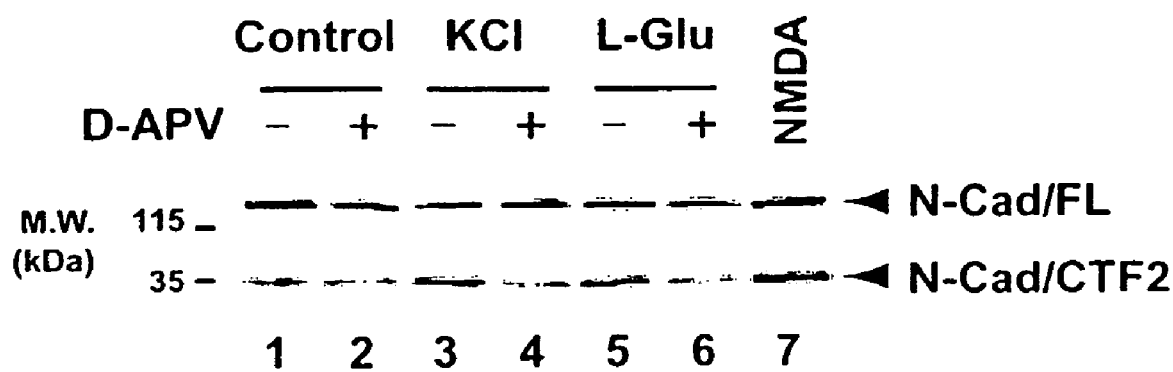

Ionomycin, an agent that stimulates calcium influx, induces the PS1/ε-cleavage of E-cadherin as demonstrated in Example 4 hereinabove. Treatment of rat primary neuronal cultures with this agent increased N-Cad/CTF2 suggesting that calcium stimulates the PS1/E-cleavage of N-cadherin. To determine whether more specific treatments that stimulate calcium influx through channels would also affect the E-cleavage of N-cadherin, the following experiment was performed. Rat brain neurons were pre-incubated in the absence (−) or presence (+) of D-APV and then stimulated with either KCl, L-glutamate (L-gly) or NMDA. Membranes from these neurons were used in in vitro assays for production of N-Cad/CTF2. FIG. 8B (lanes 1 and 3) shows that treatment of rat primary neuronal cultures with 50 mM KCl stimulated production of peptide N-Cad/CTF2.

Since high K+ depolarizes neuronal membranes resulting in neurotransmitter release at synaptic endings (Buchs and Muller (1996) Proc Nat. Acad. Sci USA 93:8040-8045), it was determined whether blocking specific postsynaptic receptors would inhibit the increase in N-Cad/CTF2. FIG. 8B (lanes 14) shows that treatment of neurons with D(−)-2-amino-5-phosphonovalerate (D-APV), a specific antagonist of the NMDA receptor, inhibited the K+-induced increase in N-Cad/CTF2, indicating involvement of this receptor in the PS1/ε-cleavage of N-cadherin. Direct stimulation of the NMDA receptor using agonist L-glutamate also induced an increase in N-Cad/CTF2 and this increase was blocked by D-APV (FIG. 8B, lanes 1, 5 and 6). Application of NMDA had similar results (FIG. 8B, lanes 1 and 7). These data indicate that the PS1/ε-cleavage of neuronal N-cadherin is stimulated by membrane depolarization and activation of the NMDA receptor.

Example 11

N-Cad/CTF2 Down-Regulates CREB-Mediated Transcription

Figure 9A:
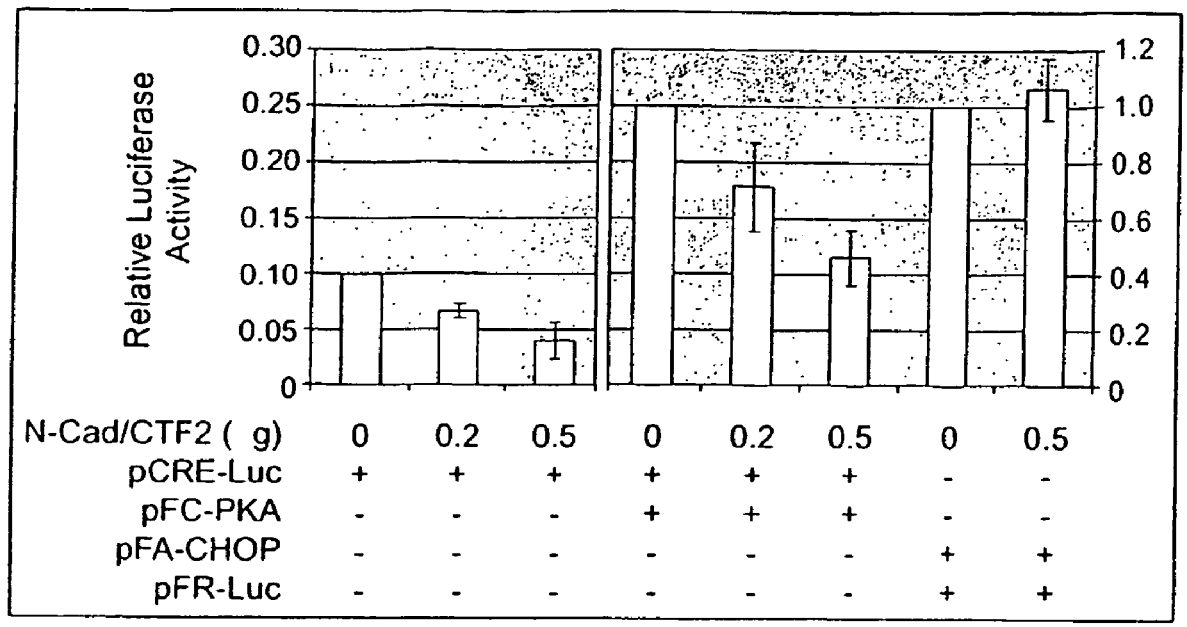
FIGS. 9A and B are bar graphs depicting the relative CRE-dependent luciferase activity in L cells transfected with increasing amounts of pN-Cad/CTF2 (FIG. 9A) and HEK293 cells transfected with PS1 (FIG. 9B).

Stimulation of synaptic NMDA receptor leads to phosphorylation of transcription factor CREB that then recruits transcription co-activator CBP, a process ultimately leading to activation of CREB-mediated gene expression (Impey and Goodman (2001) Sci STKE, PE1). The functional consequences of increased N-Cad/CTF2 production were examined to determine whether this peptide affects CRE-dependent transactivation, a process that relies on endogenous CBP and CREB. L cells were transfected with increasing amount of pN-Cad/CTF2. CRE-dependent transactivation was measured in the absence (−) or presence (+) of β-transfected PKA (pFC-PKA) using CRE-luciferase reporter plasmid (pCRE-Luc) and pSV-β-galactosidase vector. CHOP-mediated transactivation was measured by β-transfection with the Gal4-fusion trans-activator plasmids (pFA-CHOP and pFR-Luc) and pSV-β-galactosidase vector. Transfected cells were processed for luciferase activity. Results are shown in FIG. 9A.

HEK293 cultures stably transfected either with vector or WT-PS1 were co-transfected with pFC-PKA, pCRE-Luc, and pSV-β-galactosidase in the presence or absence of L-685,458 and then processed for CRE-dependent luciferase activity. Data in FIGS. 9A and B are the mean+/−s.e. of 4 experiments normalized to β-galactosidase activity and protein concentration. *, P<0.05; ***, P<0.001 (Student's t test).

Figure 9B:
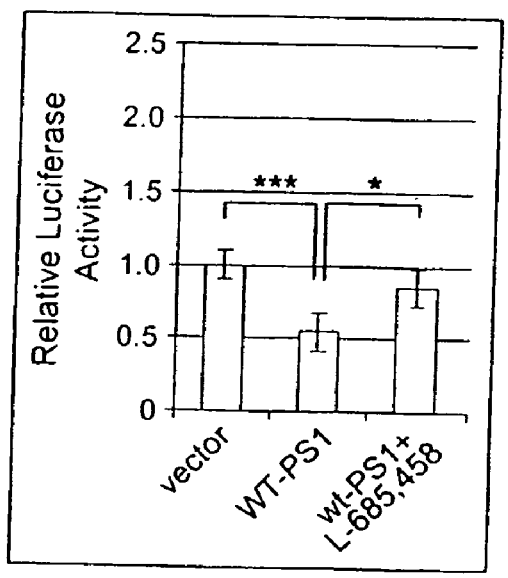
FIG. 9C depicts relative levels of c-fos or gapdh mRNAs in L cells transfected with pN-Cad/CTF2.
FIG. 9D is a Western blot depicting c-fos and N-Cad/CTF2 in L cells transfected with pN-Cad/CTF2.
Figure 9C:
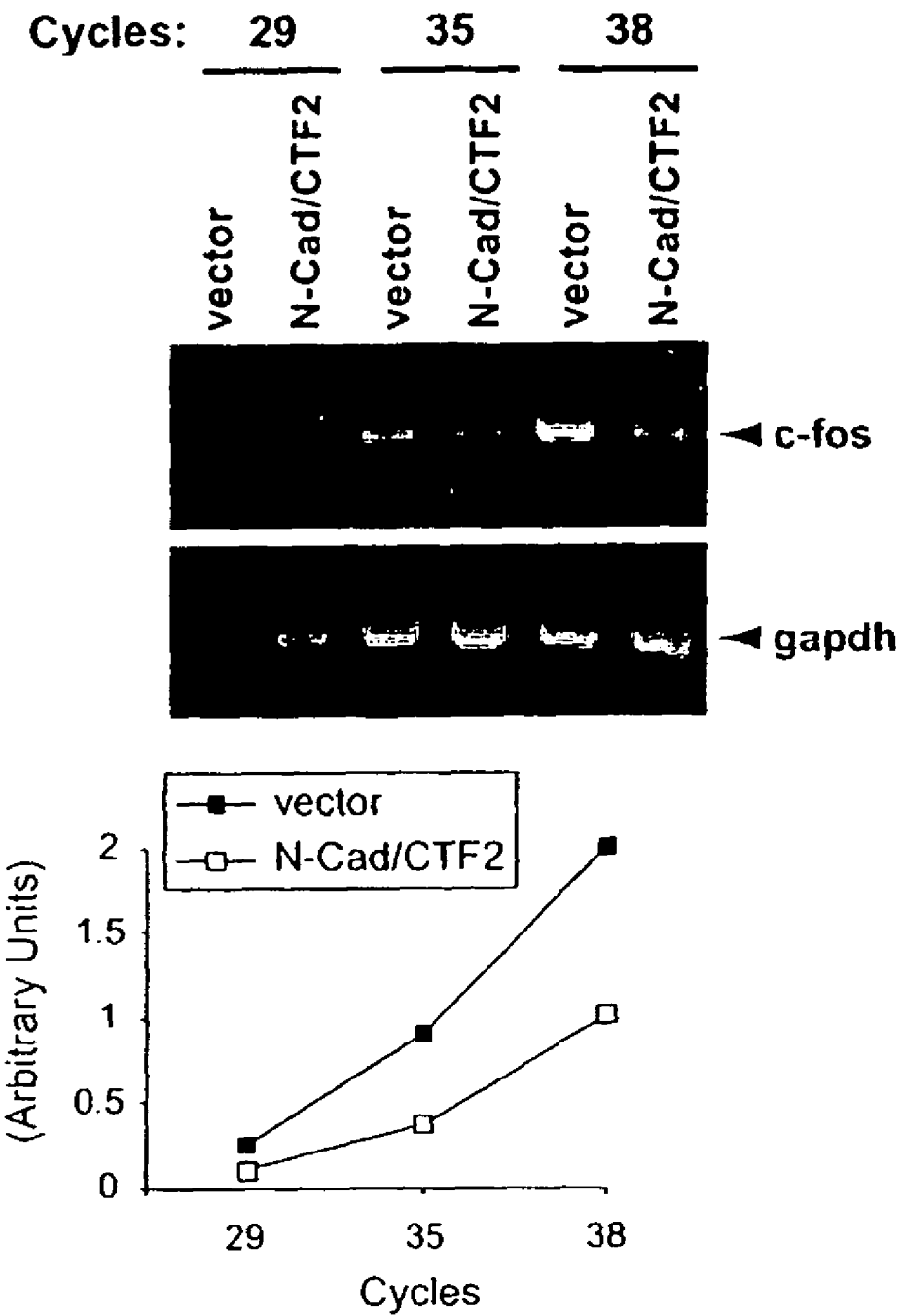

Semi-quantitative RT-PCR was used to determine relative levels of c-fos or gapdh mRNAs from L cells transfected either with vector (vector) or with 0.5 mg of pN-Cad/CTF2 (N-Cad/CTF2). The graph in FIG. 9C represents the relative abundance of c-fos-specific PCR products following quantitation of the mRNA signals shown in the upper panel.

Extracts from L cells transfected with increasing amount of pN-Cad/CTF2 were probed on WBs with anti-c-fos (FIG. 9D, upper panel), anti-β-tubulin (FIG. 9D, middle panel) or C32 (FIG. 9D, lower panel) antibodies. Bars in lower panel represent the relative amounts of c-fos protein detected on WBs shown in the upper panel.

Figure 12A:
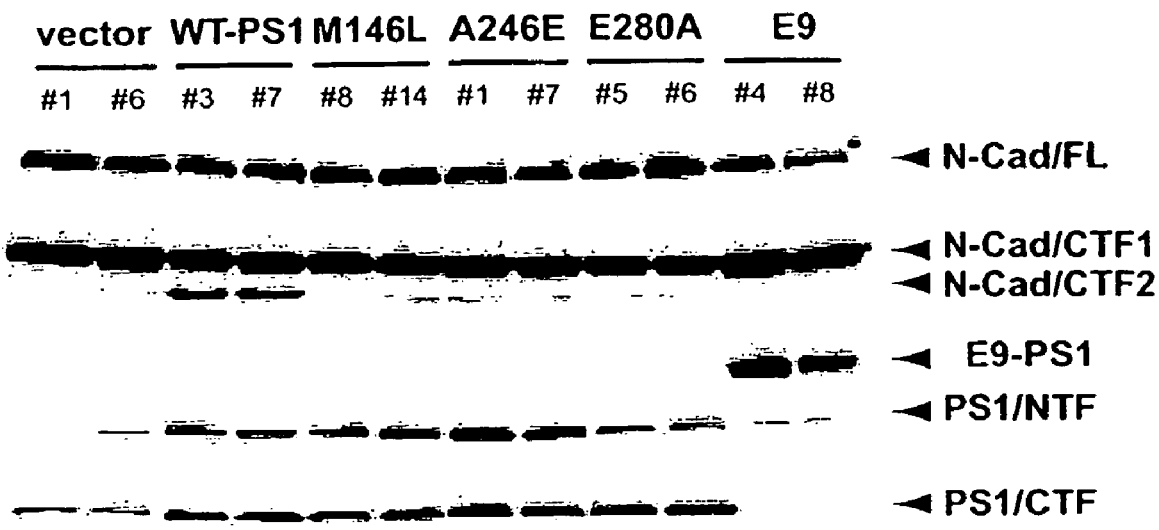
FIGS. 12A and B are Western blots of membranes of HEK293 cells transfected with WT-PS1 and PS1 mutants.
Figure 12B:
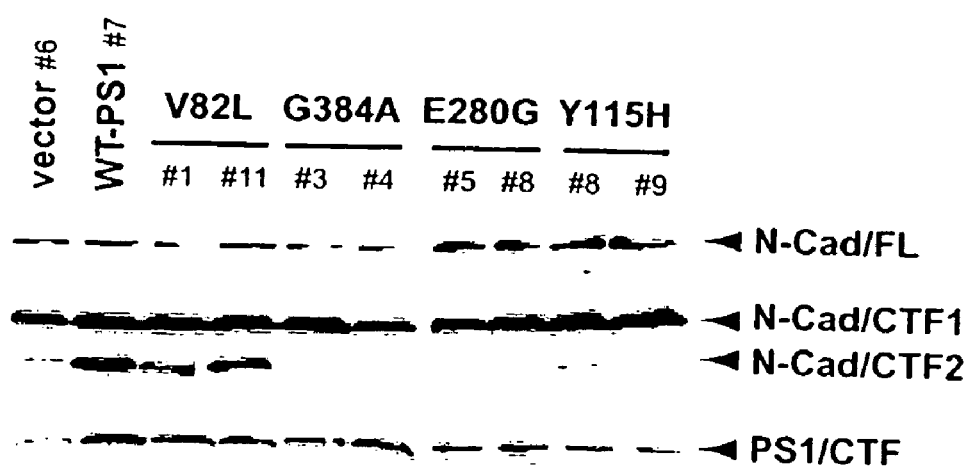
FIG. 12C shows densiometric quantitation of N-Cad/CTF2 in each mutant.
FIG. 12D depicts CRE-dependent transactivation for each mutant.
Figure 12C:
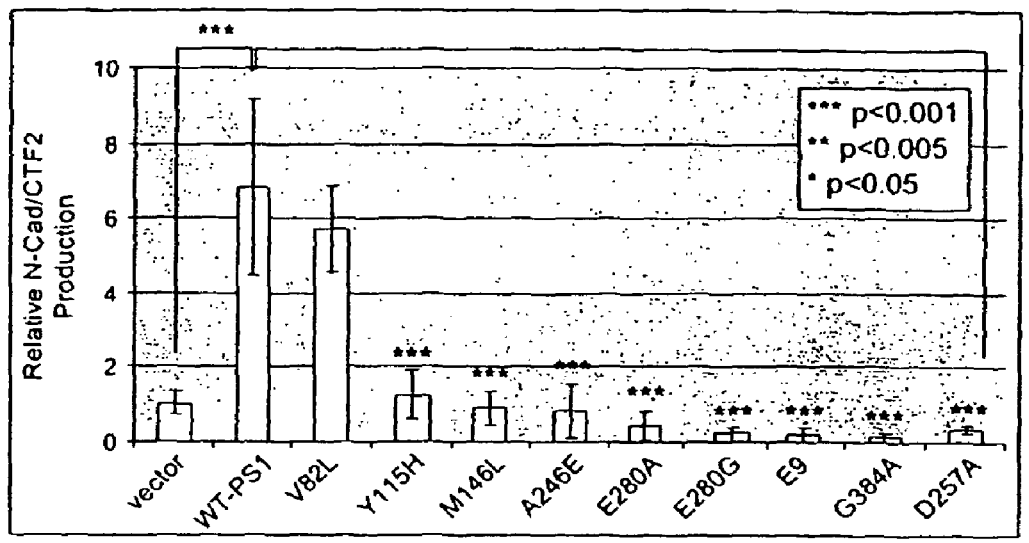
Figure 12D:
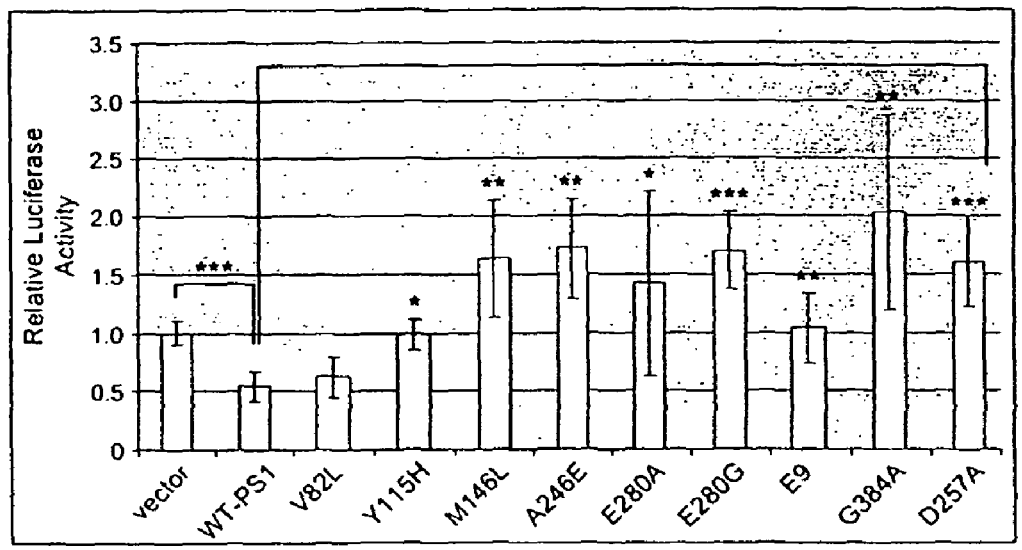

FIG. 9A shows that transfection of N-cadherin-negative L cells with N-Cad/CTF2 inhibits both constitutive and PKA-stimulated CRE-dependent transactivation in a dose-dependent manner. Transactivation by CHOP-response elements was not affected by N-Cad/CTF2 (FIG. 9A) indicating that this peptide specifically represses CRE-dependent transactivation. Since PS1 overexpression increases N-Cad/CTF2 production (FIG. 7D), these data predict that PS1 transfection should decrease CRE-dependent transactivation. Indeed, FIG. 9B shows that this is the case. PS1 overexpression decreases CRE-dependent transactivation and this decrease is reversed by γ-secretase inhibitor L-685,458 which inhibits N-Cad/CTF2 production (FIG. 7D) further supporting the suggestion that the PS1/ε-cleavage product N-Cad/CTF2 suppresses CREB-mediated transcription. Similarly, overexpression of the dominant negative mutant D257A that inhibits production of N-Cad/CTF2 (FIG. 7D) also stimulates CRE-dependent transactivation (FIG. 12D). These data show an inverse correlation between N-Cad/CTF2 production and CRE-dependent transactivation, indicating that N-Cad/CTF2 acts as a repressor of CREB-mediated transcription.

Figure 9D:
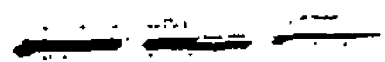
Figure 9D:
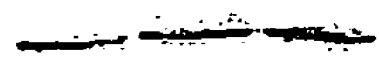
Figure 9D:
Figure 9D:
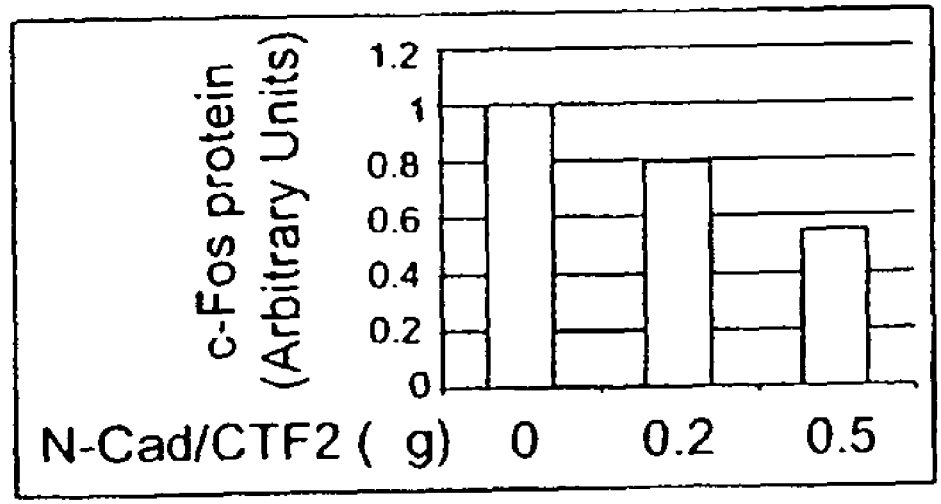

To confirm that N-Cad/CTF2 suppresses CREB-dependent transcription of endogenous genes, the expression of c-fos mRNA and protein change in response to this peptide was assessed. The c-fos promoter contains CREs and CREB is a strong regulator of the transcription of this gene (Ahn et al. (1998) Mol. Cell. Biol. 18:967-977). FIGS. 9C and 9D show that overexpression of N-Cad/CTF2 markedly reduces the amounts of cellular c-fos mRNA and c-fos protein but has no effect on the expression of gapdh mRNA or on the levels of β-tubulin suggesting that N-Cad/CTF2 specifically inhibits c-fos expression. To determine whether conditions that inhibit both PS1 activity and N-Cad/CTF2 production, like L-685,458 treatment or absence of PS1, would affect CREB-mediated transcription, the following experiment was performed.

Figure 10A:
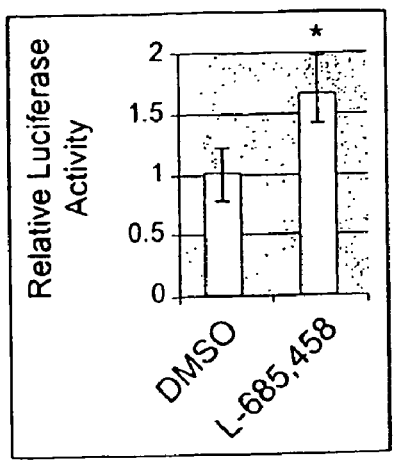
FIG. 10A is a graph depicting CRE-dependent transactivation in N2a cells incubated with DMSO or L-685,458.
Figure 10B:
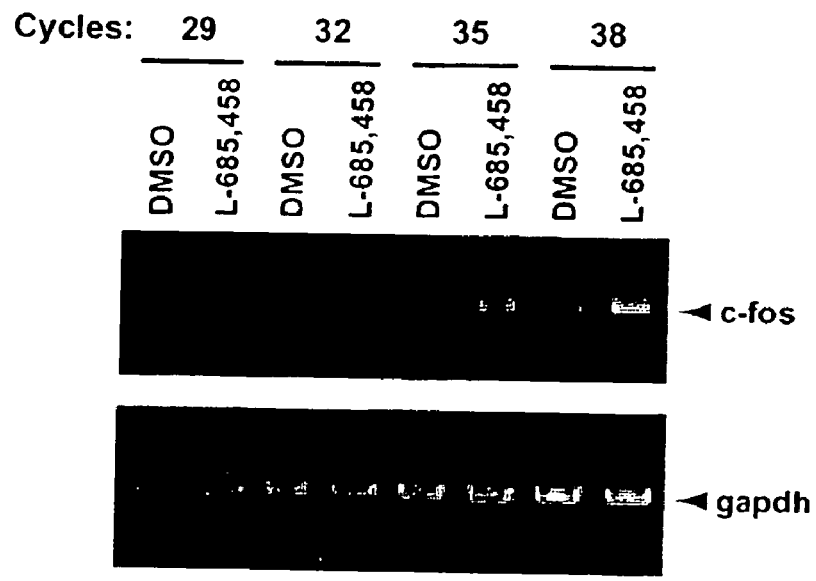
FIG. 10B depicts c-fos and gadph mRNA in N2a cells treated with DMSO or L-685,458.
Figure 10B:
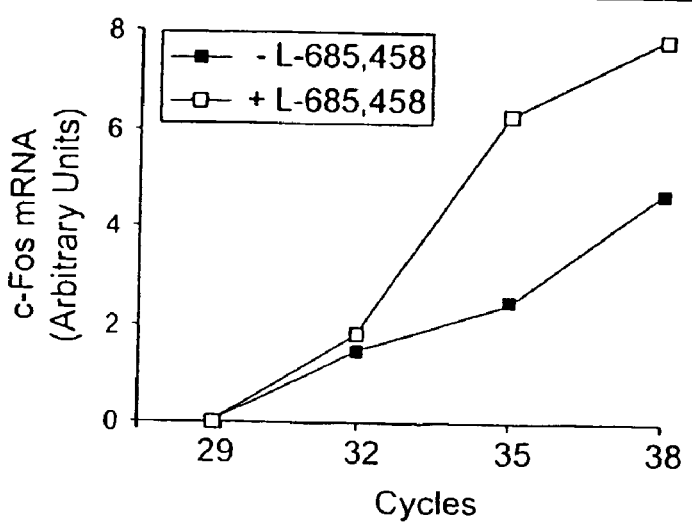
Figure 10C:
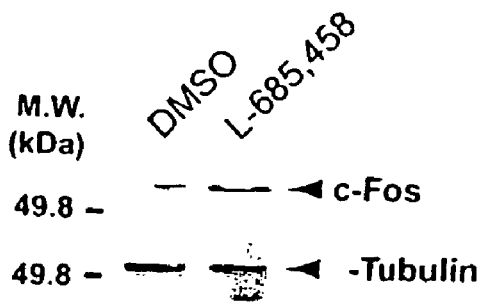
FIGS. 10C-E are Western blots depicting c-fos in extracts of N2a cells treated with DMSO or L-685,458 (FIG. 10C), extracts of PS1+/+ or PS1−/− mouse fibroblasts (FIG. 10D), and extracts of PS1+/− and PS1−/− mouse embryonic brains (FIG. 10E).
Figure 10D:
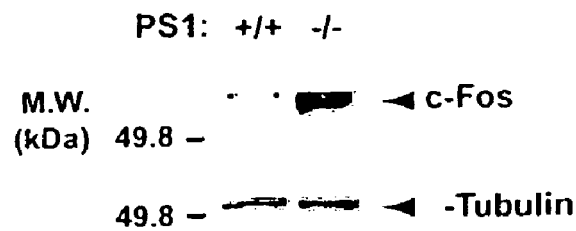

N2a cells co-transfected with plasmids pCRE-luc, pFC-PKA, and pSV-β-galactosidase were incubated for 16 hours with DMSO or with L-685,458 (0.5 mM) and CRE-dependent transactivation was measured as described above. Data in FIG. 10A are the mean+/−s.e. of 3 experiments normalized to β-galactosidase activity and protein concentration. *, P<0.05 (Student's t test). Total RNA isolated from N2a cells treated either with DMSO or with L-685,458, was analyzed by semiquantitative RT-PCR using specific primers for c-fos and gapdh. The graph in FIG. 10B represents the relative abundance of c-fos-specific PCR products following quantitation of the mRNA signals shown in the upper panel. Extract from N2a cells treated either with DMSO or with L-685,458, were probed on WBs with anti-c-fos or anti-β-tubulin antibodies. Results are shown in FIG. 10C. Extract from PS1+/+ or PS1−/− mouse fibroblasts were probed on WBs with either anti-c-fos or anti-β-tubulin antibodies. Results are shown in FIG. 10D. Extract from PS1+/− or PS1−/− mouse embryonic brains were probed on WBs with anti-c-fos (FIG. 10E, upper panel), anti-b-tubulin (FIG. 10E, middle panel), or anti-PS1/CTF (FIG. 10E, lower panel) antibodies.

Figure 10E:
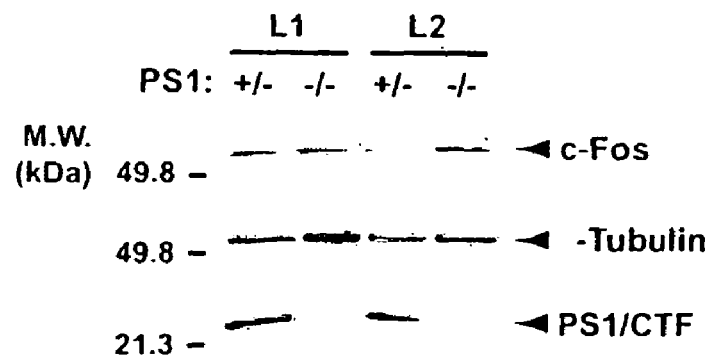

L-685,458 treatment of N2a cells increased CRE-dependent transactivation (FIG. 10A) and stimulated c-fos mRNA (FIG. 10B) and c-fos protein (FIG. 10C) beyond the levels observed in untreated controls, whereas gapdh mRNA and β-tubulin remained unchanged (FIGS. 10B and 10C). Furthermore, FIGS. 10D and 10E show that absence of PS1 results in abnormally high levels of c-fos protein in both fibroblast cultures and mouse brain while levels of β-tubulin remain unchanged. Together, these data show that downregulation of PS1 activity results in a decreased production of N-Cad/CTF2 and in a specific overexpression of c-fos indicating that PS1 activity is needed for maintaining normal expression of this gene.

Example 12

N-Cad/CTF2 Binds and Sequesters CBP in the Cytoplasm

Figure 11A:
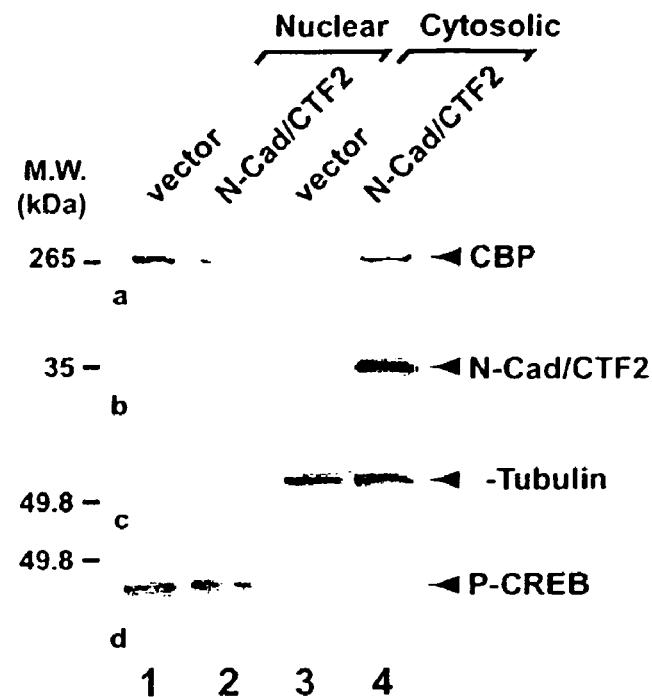
FIGS. 11A and B are Western blots of L cells transfected with pN-Cad/CTF2.
Figure 11B:
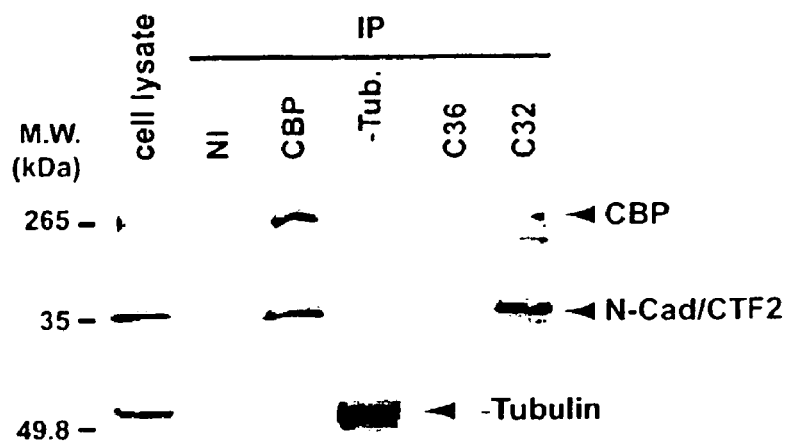
FIG. 11C depicts the results of an electrophoretic mobility shift assay that examined the effect of N-Cad/CTF2 on the formation of a CBP/CREB/DNA complex.
Figure 11C:
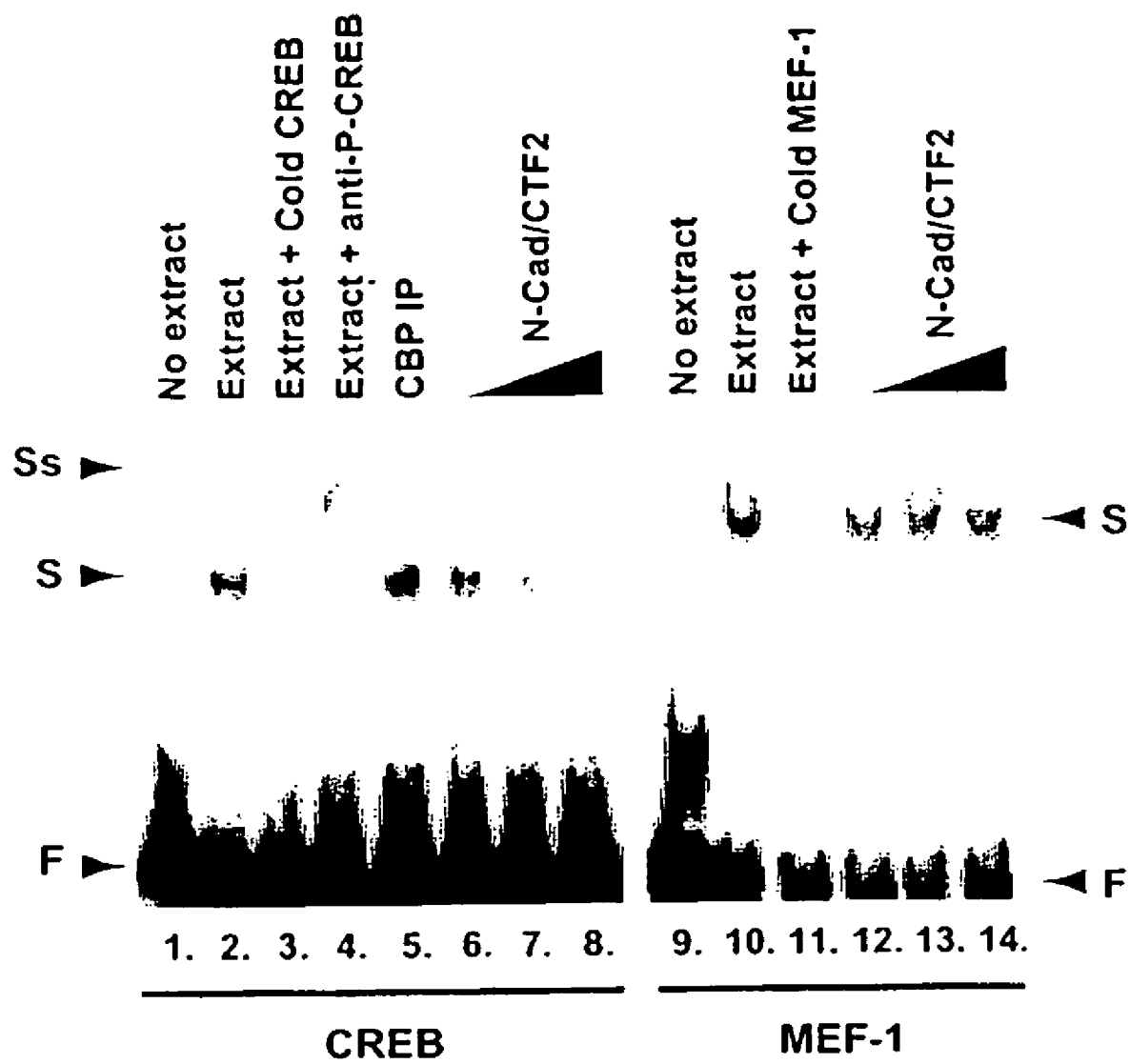

To determine how N-Cad/CTF2 affects CREB-mediated transcription, the following experiments were performed. L cells transfected either with vector (vector) or pN-Cad/CTF2 (N-Cad/CTF2) plasmids were fractionated into nuclear and cytosolic fractions, and probed on WBs with anti-CBP (FIG. 11A, panel a), anti-N-cadherin (FIG. 11A, panel b), anti-β-tubulin (FIG. 11A, panel c) or anti-phosphorylated CREB (P-CREB; FIG. 11A, panel d) antibodies. Extract from pN-Cad/CTF2-transfected L cells was immunoprecipitated either with non-immune serum (NI) or with antibodies against CBP (CBP), β-tubulin (β-Tub), E-cadherin (C36) or N-cadherin (C32). Obtained IPs were probed with anti-CBP (FIG. 11B, upper panel), anti-N-cadherin (FIG. 11B, middle panel) or anti-β-tubulin (FIG. 11B, lower panel) antibodies. For reference, cell lysate was also probed (FIG. 11B, first lane). L cells transiently transfected with pN-Cad/CTF2 were analyzed by immunofluorescence staining. Cells were triple-labeled with DAPI (blue), anti-CBP (red) and anti-N-cadherin (C32; green) antibodies. Nuclear extract from pN-Cad/CTF2-transfected L cells were incubated with biotinylated double-stranded DNA probes containing binding sequence for either CREB (FIG. 11C, left panel) or MEF-1 (FIG. 11C, right panel). The lanes in FIG. 11C are as follows: Lanes 1 and 9: probes alone; Lanes 2 and 10: probe plus extract; Lanes 3 and 11: samples as in lanes 2 and 10 plus a 60-fold excess of unlabelled (cold) probes used as competitors; Lane 4: incubation was carried out in the presence of anti-phosphorylated CREB-Ser133 antibody 1B6; Lane 5: nuclear extract was immunoprecipitated with anti-CBP antibody A-22 and the obtained IPs were eluted with sodium deoxycholate, incubated with CREB probe and loaded on the gel; Lanes 6-8 and 12-14: nuclear extract from cells transfected without (lanes 6 and 12) or with 0.2 μg (lanes 7 and 13) and 0.5 μg (lanes 8 and 14) of pN-Cad/CTF2 were incubated either with CREB (lanes 6-8) or MEF-1 (lanes 12-14) probes and then loaded on the gel. F indicates free probes. Shifted probes (S) were competed out with unlabeled probes (lanes 3 and 11). CREB probe was supershifted (Ss) with antibody against phosphorylated CREB (lane 4) and the shifted CREB probe was also obtained after immunoprecipitation of nuclear extracts with CBP antibody (lane 5), indicating that the DNA-bound complex contains both CREB and CBP.

CREB-mediated transcription is stimulated by phosphorylation of CREB-Ser133 and CBP recruitment to transcription initiation complexes formed at CRE-containing promoters (Vo and Goodman (2001) J. Biol. Chem. 276:13505-13508. However, any change of CREB phosphorylation in response to N-Cad/CTF2 overexpression was not detected. (FIG. 11A, panel d). The ability of this peptide to affect CREB-mediated transcription by limiting the availability of CBP was assessed. Cell fractionation and biochemical studies showed that as expected (Chrivia et al. (1993) Nature 365:855-854), in vector-transfected cells, CBP was found only in the nuclear fraction where phosphorylated CREB is also found (FIG. 11A, lanes 1 and 3, panels a and d). Following transfection with N-Cad/CTF2, however, nuclear CBP decreased with a concomitant increase in cytosolic CBP, indicating that in the presence of N-Cad/CTF2, CBP translocates to the cytoplasm where N-Cad/CTF2 is localized (FIG. 11A, panels a and b). In contrast to CBP, N-Cad/CTF2 had no effects on the localization of phosphorylated CREB, which remained in the nucleus (FIG. 11A, panel d). Additional experiments showed that in N-Cad/CTF2-transfected cells, CBP co-immunoprecipitates with N-Cad/CTF2 but not with β-tubulin. The reverse is also true, N-Cad/CTF2 co-immunoprecipitates with CBP (FIG. 11B). These data indicate that the two proteins form a complex in the cytoplasm. In agreement with the biochemical and immunoprecipitation studies, two-color immunofluorescence staining showed that compared to non-transfected controls which display no CBP staining in the cytoplasm, cells transfected with N-Cad/CTF2 show a clear cytoplasmic staining for both N-Cad/CTF2 and CBP. In contrast to CBP, CREB staining remained nuclear and showed no co-localization with N-Cad/CTF2 staining in the transfected cells. Electrophoretic mobility shift assays (EMSA) were used to examine the effects of N-Cad/CTF2 on formation of a CBP/CREB complex on its cognate CRE motif. FIG. 11C (lanes 6-8) shows that nuclear extract from N-Cad/CTF2-transfected cells are defective in their ability to promote formation of a CBP/CREB complex on CRE-containing DNA templates. In contrast, N-Cad/CTF2 transfection had no effect on the ability of this nuclear extract to promote complex formation between transcription factor MEF-1 and a DNA probe containing MEF-1-binding elements (FIG. 11C, lanes 12-14). Together, these data show that N-Cad/CTF2 binds with CBP and sequesters it to the cytoplasm thus limiting its availability for formation of nuclear CREB/CBP/DNA complexes.

Example 13

PS1 FAD Mutants do not Stimulate N-Cad/CTF2 Production and are Unable to Suppress CREB-Mediated Transcription To examine the effects of PS1 FAD mutations on the ε-cleavage of N-cadherin, the amounts of N-Cad/CTF2 produced in the in vitro assay using membranes from HEK293 cells over-expressing comparable levels of either WT or PS1 FAD mutants were measured. Membranes from two independent clones of HEK293 cells each stably transfected with vector alone (FIG. 12A, #1 and 6), WT-PS1 (FIG. 12A, #3 and 7), or with PS1 mutants M146L (FIG. 12A, #8 and 14), A246E (FIG. 12A, #1 and 7), E280A (FIG. 12A, #5 and 6), ΔE9 (FIG. 12A, #4 and 8), V82L (FIG. 12B, #1 and 11), G384A (FIG. 12B, #3 and 4), E280G (FIG. 12B, #5 and 8) and Y115H (FIG. 12B, #8 and 9) were incubated in vitro and produced N-Cad/CTF2 was detected on WBs with C32 (FIGS. 12A and B, upper panels). Numbers correspond to isolated clones. PS1 fragments were detected with R222 (FIG. 12A, middle panel) or 33B10 (FIGS. 12A and B, lower panels). FIG. 12C depicts combined densitometric quantitation of N-Cad/CTF2 using two independent clones of each mutant (FIGS. 12, A and B). N-Cad/CTF2 levels were normalized to N-Cad/CTF2 produced from vector-transfected cells. Bars represent the mean+/−s.e. of three independent experiments using two clones for each mutant. CRE-dependent transactivation was measured using two independent HEK293 cell stable clones of each mutant (FIGS. 12, A and B). All clones were co-transfected with pFC-PKA, pCRE-Luc, and pSV-β-galactosidase. Luciferase activity data were normalized to β-galactosidase activity and protein concentration. Results are shown in FIG. 12D. Bars represent the mean+/−s.e. of three experiments. *, $P<0.05$; , $P<0.005$; *, $P<0.001$ (Student's t test).

FIGS. 12A, B and C show that membranes from HEK293 cell cultures overexpressing WT PS1 produce approximately seven times as much N-Cad/CTF2 as the vector-transfected controls. In contrast, membranes from HEK293 cell cultures each overexpressing a PS1 FAD mutant carrying one of the missense mutations Y115H, M146L, A246E, E280A, E280G and G384A or the deletion mutation ΔE9, showed no increase in N-Cad/CTF2 production indicating that these mutations are strong inhibitors of the PS1-dependent ε-cleavage of N-cadherin. PS1 FAD mutant V82L was the only mutant that showed substantial E-cleavage although it was less active than the WT PS1 (FIGS. 12, B and C).

That FAD mutations inhibit production of N-Cad/CTF2, a peptide that binds CBP and suppresses CREB-mediated transcription, predicts that PS1 FAD mutants should be defective in their ability to suppress CRE-dependent transactivation. Indeed, FIG. 12D shows that although overexpression of WT PS1 significantly suppressed CRE-dependent transactivation, PS1 FAD mutants Y115H, M146L, A246E, E280A, E280G, ΔE9 and G384A are unable to inhibit CRE transactivation. FAD mutants M146L, A246E, E280G and G384A as well as the γ-secretase dominant negative mutant D257A showed a clear dominant positive effect, increasing CRE-dependent transactivation over that of the vector control (FIG. 12D). In agreement with its effects on N-Cad/CTF2 production, overexpression of FAD mutant PS1 V82L failed to increase significantly the CRE-dependent transactivation compared to WT PS1 transfected controls. This FAD mutant does not significantly increase production of Aβ42 peptide in cell cultures either (Murayama et al. (1999) Neuro Sci. Len. 265:61-63). The inverse correlation between the effects of PS1 mutants on N-Cad/CTF2 production and CRE-dependent transactivation, observed in all cases, indicates that these mutants over-stimulate transcription by inhibiting production of N-Cad/CTF2.

Figure 13A:
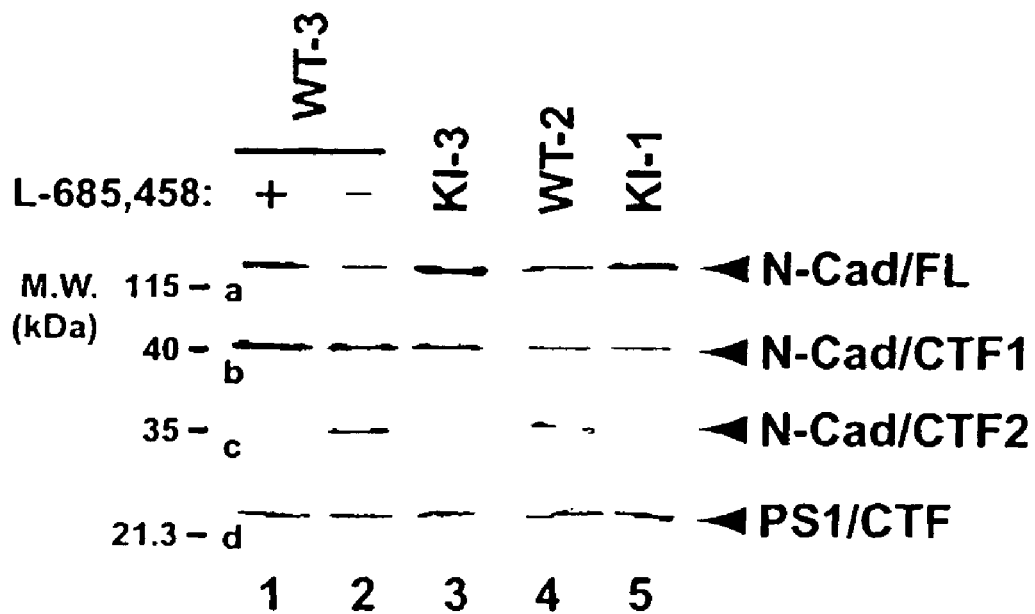
FIGS. 13A and B are Western blots of membranes (FIG. 13A) and protein extracts (FIG. 13B) from embryonic fibroblast culture of wild type and PS1 P264L knock-in mice.
Figure 13B:
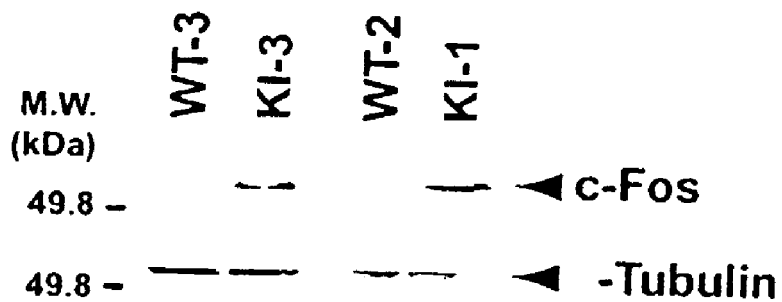
FIG. 13C is a schematic representation of the effects of PS1/ε-cleavage of N-cadherin on CBP/CREB signaling.

To investigate the consequences of FAD mutations in a physiologically relevant system in the absence of PS1 overexpression, the ε-cleavage of N-cadherin was examined in two independent embryonic fibroblast clones derived from a gene-targeted (knock-in) mouse homozygous for the human PS1 FAD mutation P264L (Siman et al. (2000) J. Neurosci. 20:8717-8726). Expression of the knock-in mutant PS1 allele is under the control of the endogenous PS1 gene. These models are distinct from overexpressing transgenic models because the mutant gene is expressed at normal levels, similar to those observed in WT models (FIG. 13, panel d). As controls, two WT fibroblast cell lines independently derived from WT littermates were used. Membranes from embryonic fibroblast cultures isolated either from PS1 P264L homozygous knock-in mice (KI-3 and KI-1) or from WT littermates (WT-3 and WT-2) were processed for the generation of N-Cad/CTF2. Following incubation, membranes were probed with C32 (FIG. 13A, panels a-c) or 33B10 (FIG. 13A, panel d). Protein extract either from WT (WT-3 and WT-2) or from PS1 P264L knock-in (KI-3 and KI-1) fibroblasts were probed on WBs with anti-c-fos (FIG. 13B, upper panels) and anti-b-tubulin (FIG. 13B, lower panels) antibodies.

Figure 13C:
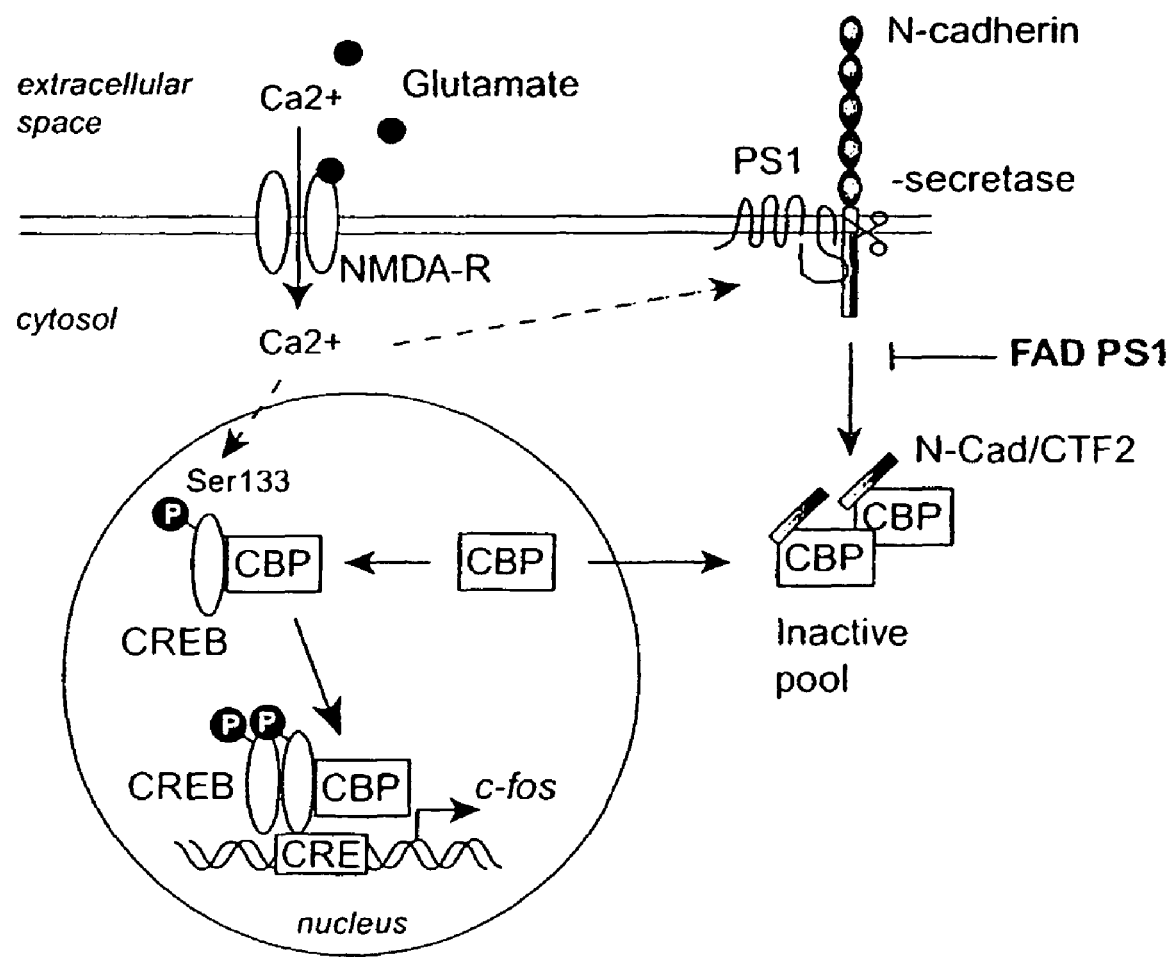

Production of N-Cad/CTF2 was sensitive to γ-secretase inhibitor L-685,458 (FIG. 13A, lanes 1 and 2). FIG. 13A (lanes 2-5) shows that samples from the knock-in fibroblast cell lines produced undetectable amounts of N-Cad/CTF2 compared to samples from the WT clones, indicating that this FAD mutation also inhibits the γ-cleavage of N-cadherin. Furthermore, the PS1 P264L knock-in cells contained significantly higher levels of endogenous c-fos compared to WT controls, although β-tubulin levels remained unchanged (FIG. 13B). Thus, the PS1 FAD mutation P264L inhibits N-Cad/CTF2 production and increases the cellular levels of c-fos protein above those detected in normal controls indicating that this mutation induces a dysregulation of c-fos expression by inhibiting the PS1/ε-secretase activity. FIG. 13C is a schematic representation of the effects of the PS1/e-cleavage of N-cadherin on CBP/CREB signaling. This cleavage releases N-cadherin ICD N-Cad/CTF2 that binds CBP and sequesters it to the cytoplasm thus downregulating CREB-mediated transcription. PS1 FAD mutations inhibit N-Cad/CTF2 production and stimulate CBP/CREB-dependent transcription. In neuronal cells, the c-cleavage is stimulated by NMDA receptor activation.

We claim:

1. A peptide that binds to presenilin-1 and comprises the sequence EGGGE (SEQ ID NO: 5) wherein the peptide is from five to fifteen amino acids in length.

2. The peptide of claim 1 comprising a sequence selected from the group consisting of EGGGEEDQDFDL (SEQ ID NO: 1), EGGGEMDTTSYD (SEQ ID NO: 2), EGGGEEDQDYDLS (SEQ ID NO: 3) and EGGGEED (SEQ ID NO: 4).

3. A composition comprising the peptide of claim 1.

4. A method of inhibiting Presenilin-1-mediated γ-secretase activity comprising contacting a cell capable of exhibiting such activity with the composition of claim 1.

* * * * *

UNITED STATES PATENT AND TRADEMARK OFFICE
CERTIFICATE OF CORRECTION

PATENT NO. : 7,884,067 B2
APPLICATION NO. : 10/509170
DATED : February 8, 2011
INVENTOR(S) : Nikolaos Robakis et al.

It is certified that error appears in the above-identified patent and that said Letters Patent is hereby corrected as shown below:

At column 1, line number 15, please delete "Grant Nos. AG-08200, AG-05138 and AG-17926" and replace it with --Grant Nos. AG-008200, AG-005138 and AG-017926-- therefor.

At column 1, line numbers 16-17, please delete "may have certain rights" and insert --has certain rights-- therefor.

Signed and Sealed this
Nineteenth Day of July, 2011

David J. Kappos
*Director of the United States Patent and Trademark Office*

SEQUENCE LISTING

```
<160> NUMBER OF SEQ ID NOS: 19

<210> SEQ ID NO 1
<211> LENGTH: 12
<212> TYPE: PRT
<213> ORGANISM: Homo sapiens

<400> SEQUENCE: 1

Glu Gly Gly Gly Glu Glu Asp Gln Asp Phe Asp Leu
1               5                   10

<210> SEQ ID NO 2
<211> LENGTH: 12
<212> TYPE: PRT
<213> ORGANISM: Homo sapiens

<400> SEQUENCE: 2

Glu Gly Gly Gly Glu Met Asp Thr Thr Ser Tyr Asp
1               5                   10

<210> SEQ ID NO 3
```

```
<211> LENGTH: 13
<212> TYPE: PRT
<213> ORGANISM: Homo sapiens

<400> SEQUENCE: 3

Glu Gly Gly Gly Glu Glu Asp Gln Asp Tyr Asp Leu Ser
1               5                   10

<210> SEQ ID NO 4
<211> LENGTH: 7
<212> TYPE: PRT
<213> ORGANISM: Homo sapiens

<400> SEQUENCE: 4

Glu Gly Gly Gly Glu Glu Asp
1               5

<210> SEQ ID NO 5
<211> LENGTH: 5
<212> TYPE: PRT
<213> ORGANISM: Homo sapiens

<400> SEQUENCE: 5

Glu Gly Gly Gly Glu
1               5

<210> SEQ ID NO 6
<211> LENGTH: 20
<212> TYPE: PRT
<213> ORGANISM: Homo sapiens

<400> SEQUENCE: 6

Cys Glu Gly Ala Ala Gln Val Cys Arg Lys Ala Gln Pro Val Glu Ala
1               5                   10                  15

Gly Leu Gln Ile
            20

<210> SEQ ID NO 7
<211> LENGTH: 21
<212> TYPE: PRT
<213> ORGANISM: Homo sapiens

<400> SEQUENCE: 7

Cys Asp Ser Asn Gly Asp Cys Thr Asp Val Asp Arg Ile Val Gly Ala
1               5                   10                  15

Gly Leu Gly Thr Gly
            20

<210> SEQ ID NO 8
<211> LENGTH: 21
<212> TYPE: PRT
<213> ORGANISM: Homo sapiens

<400> SEQUENCE: 8

Lys Cys Asn Glu Gln Gly Glu Phe Thr Phe Cys Glu Asp Met Ala Ala
1               5                   10                  15

Gln Val Gly Val Ser
            20

<210> SEQ ID NO 9
<211> LENGTH: 11
<212> TYPE: PRT
<213> ORGANISM: Homo sapiens
```

```
<400> SEQUENCE: 9

Lys Ala Gln Pro Val Glu Ala Gly Leu Gln Ile
1               5                   10

<210> SEQ ID NO 10
<211> LENGTH: 5
<212> TYPE: PRT
<213> ORGANISM: Homo sapiens

<400> SEQUENCE: 10

Gln Pro Val Glu Ala
1               5

<210> SEQ ID NO 11
<211> LENGTH: 14
<212> TYPE: PRT
<213> ORGANISM: Homo sapiens

<400> SEQUENCE: 11

Val Glu Ala Gly Leu Gln Ile Pro Ala Ile Leu Gly Ile Leu
1               5                   10

<210> SEQ ID NO 12
<211> LENGTH: 11
<212> TYPE: PRT
<213> ORGANISM: Homo sapiens

<400> SEQUENCE: 12

Arg Arg Arg Ala Val Val Lys Glu Pro Leu Leu
1               5                   10

<210> SEQ ID NO 13
<211> LENGTH: 20
<212> TYPE: DNA
<213> ORGANISM: Homo sapiens

<400> SEQUENCE: 13
gggtttcaac gccgactacg                                          20

<210> SEQ ID NO 14
<211> LENGTH: 20
<212> TYPE: DNA
<213> ORGANISM: Homo sapiens

<400> SEQUENCE: 14
cagcttggga aggagtcagc                                          20

<210> SEQ ID NO 15
<211> LENGTH: 18
<212> TYPE: DNA
<213> ORGANISM: Homo sapiens

<400> SEQUENCE: 15
tgtcgtggag tctactgg                                            18

<210> SEQ ID NO 16
<211> LENGTH: 18
<212> TYPE: DNA
<213> ORGANISM: Homo sapiens

<400> SEQUENCE: 16
cagcatcaaa ggtggagg                                            18
```

```
<210> SEQ ID NO 17
<211> LENGTH: 27
<212> TYPE: DNA
<213> ORGANISM: Homo sapiens

<400> SEQUENCE: 17
agagattgcc tgacgtcaga gagctag                                          27

<210> SEQ ID NO 18
<211> LENGTH: 25
<212> TYPE: DNA
<213> ORGANISM: Homo sapiens

<400> SEQUENCE: 18
gatcccccca acacctgctg cctga                                            25

<210> SEQ ID NO 19
<211> LENGTH: 72
<212> TYPE: PRT
<213> ORGANISM: Homo sapiens

<400> SEQUENCE: 19

Gln Pro Val Glu Ala Gly Leu Gln Ile Pro Ala Ile Leu Gly Ile Leu
1               5                   10                  15

Gly Gly Ile Leu Ala Leu Leu Ile Leu Ile Leu Leu Leu Leu Leu Phe
            20                  25                  30

Leu Arg Arg Arg Ala Val Val Lys Glu Pro Leu Leu Pro Pro Glu Asp
        35                  40                  45

Asp Thr Arg Asp Asn Val Tyr Tyr Asp Glu Glu Gly Gly Gly Glu
    50                  55                  60

Glu Asp Gln Asp Phe Asp Leu Ser
65                  70
```